(12) United States Patent
Girouard

(10) Patent No.: US 10,349,902 B2
(45) Date of Patent: Jul. 16, 2019

(54) METHOD AND APPARATUS FOR COMMUNICATION BETWEEN A SENSOR AND A MANAGING DEVICE

(71) Applicant: Brain Sentinel, Inc., San Antonio, TX (US)

(72) Inventor: Michael R. Girouard, San Antonio, TX (US)

(73) Assignee: Brain Sentinel, Inc., San Antonio, TX (US)

( * ) Notice: Subject to any disclaimer, the term of this patent is extended or adjusted under 35 U.S.C. 154(b) by 953 days.

(21) Appl. No.: 14/852,745

(22) Filed: Sep. 14, 2015

(65) Prior Publication Data

US 2016/0080107 A1    Mar. 17, 2016

Related U.S. Application Data

(60) Provisional application No. 62/050,054, filed on Sep. 12, 2014.

(51) Int. Cl.
*A61B 5/00* (2006.01)
*H04L 1/00* (2006.01)
(Continued)

(52) U.S. Cl.
CPC ............ *A61B 5/746* (2013.01); *A61B 5/0004* (2013.01); *A61B 5/0022* (2013.01);
(Continued)

(58) Field of Classification Search
CPC ..... A61B 5/746; A61B 5/0004; A61B 5/0022; A61B 5/7275; A61B 5/0488;
(Continued)

(56) References Cited

U.S. PATENT DOCUMENTS 5,269,302 A * 12/1993 Swartz ................. A61N 1/38
607/45
5,476,488 A * 12/1995 Morgan ............... A61B 5/0031
128/903
(Continued)

FOREIGN PATENT DOCUMENTS

CN   101227209 A   7/2008
EP   2123221 A3    9/2013
JP   10-22945 A    1/1998

OTHER PUBLICATIONS

International Search Report and Written Opinion dated Dec. 4, 2015 issued in International App. No. PCT/US2015/049859 (7 pages).
(Continued)

*Primary Examiner* — Rene T Towa
(74) *Attorney, Agent, or Firm* — Pizarro Allen PC

(57) ABSTRACT

Methods are described herein for adjusting characteristics of signals used to verify or track the reliability of communication between a remote sensor and a managing device. For example, an exchange rate of signals sent between the remote sensor and managing device may be adjusted to minimize power consumption when the devices are determined to be reliably communicating. In some embodiments, apparatuses and methods herein may further be configured to inform an individual of when a remote sensor approaches a physical boundary, moves out of a communication range, is turned off, becomes damaged, or otherwise has or may become incapable of proper or reliable communication.

16 Claims, 8 Drawing Sheets

(51) Int. Cl.
*H04Q 9/00* (2006.01)
*H04W 4/24* (2018.01)
*G16H 50/30* (2018.01)
*H04W 52/02* (2009.01)
*H04W 52/04* (2009.01)
*A61B 5/0488* (2006.01)

(52) U.S. Cl.
CPC .......... *A61B 5/0488* (2013.01); *A61B 5/4094* (2013.01); *A61B 5/7275* (2013.01); *G16H 50/30* (2018.01); *H04Q 9/00* (2013.01); *H04W 4/24* (2013.01); *H04W 52/0245* (2013.01); *H04W 52/04* (2013.01); *A61B 2560/0209* (2013.01); *H04L 1/0001* (2013.01); *H04Q 2209/40* (2013.01); *H04W 52/0254* (2013.01); *Y02D 70/00* (2018.01); *Y02D 70/142* (2018.01); *Y02D 70/144* (2018.01); *Y02D 70/164* (2018.01)

(58) Field of Classification Search
CPC ......... A61B 5/4094; A61B 2560/0209; H04W 4/24; H04W 52/0245; H04W 52/04; H04W 52/0254; G06F 19/00; H04Q 9/00; H04Q 2209/40; Y02D 70/00; Y02D 70/144; Y02D 70/164; Y02D 70/142; H04L 1/0001
See application file for complete search history.

(56) References Cited

U.S. PATENT DOCUMENTS

| | | | |
|---|---|---|---|
| 5,513,646 A | 5/1996 | Lehrman et al. | |
| 6,147,618 A | 11/2000 | Halleck et al. | |
| 6,307,481 B1 | 10/2001 | Lehrman et al. | |
| 6,369,713 B1 | 4/2002 | Halleck et al. | |
| 6,377,185 B1 | 4/2002 | Halleck et al. | |
| 6,415,033 B1 | 7/2002 | Halleck et al. | |
| 6,416,483 B1 | 7/2002 | Halleck et al. | |
| 6,501,386 B2 | 12/2002 | Lehrman et al. | |
| 6,575,916 B2 | 6/2003 | Halleck et al. | |
| 6,661,347 B2 | 12/2003 | Lehrman et al. | |
| 6,666,830 B1 | 12/2003 | Lehrman et al. | |
| 6,703,939 B2 | 3/2004 | Lehrman et al. | |
| 6,706,002 B1 | 3/2004 | Halleck et al. | |
| 6,734,802 B2 | 5/2004 | Halleck et al. | |
| 6,864,796 B2 | 3/2005 | Lehrman et al. | |
| 6,935,335 B1 | 8/2005 | Lehrman et al. | |
| 6,947,565 B2 | 9/2005 | Halleck et al. | |
| 6,978,149 B1 | 12/2005 | Morelli et al. | |
| 7,066,894 B2 | 6/2006 | Halleck et al. | |
| 7,095,331 B2 | 8/2006 | Lehrman et al. | |
| 7,145,461 B2 | 12/2006 | Lehrman et al. | |
| 7,479,890 B2 | 1/2009 | Lehrman et al. | |
| 7,789,837 B2 | 9/2010 | Lehrman et al. | |
| 8,740,805 B2 | 6/2014 | Lehrman et al. | |
| 9,375,143 B2 | 6/2016 | Matsuno et al. | |
| 2005/0249157 A1* | 11/2005 | Qian | H04L 43/0829 370/329 |
| 2007/0203986 A1* | 8/2007 | Krishnan | H04L 43/00 709/206 |
| 2008/0001735 A1 | 1/2008 | Tran | |
| 2009/0029652 A1 | 1/2009 | Xie et al. | |
| 2009/0171168 A1 | 7/2009 | Leyde et al. | |
| 2009/0201172 A1 | 8/2009 | Edell, Jr. | |
| 2010/0137735 A1 | 6/2010 | Hoppe | |
| 2010/0198098 A1 | 8/2010 | Osorio et al. | |
| 2010/0274100 A1* | 10/2010 | Behar | A61B 5/0002 600/301 |
| 2012/0108999 A1* | 5/2012 | Leininger | A61B 5/0004 600/546 |
| 2012/0210150 A1 | 8/2012 | De Lind Van Wijngaarden et al. | |
| 2012/0310050 A1* | 12/2012 | Osorio | A61B 5/4094 600/300 |
| 2013/0012830 A1 | 10/2013 | Leininger et al. | |
| 2014/0163413 A1* | 6/2014 | Conradsen | A61B 5/04004 600/546 |

OTHER PUBLICATIONS

Ikram, Waqas, "Adaptive Multi-Channel Transmission Power Control for Industrial Wireless Instrumentation" IEEE Transactions on Industrial Informatics, vol. 10 No. 2, May 2014 pp. 978-990 (13 Pages).

Xiao, Shuo et al. "Adapting Radio Transmit Power in Wireless Body Area Sensor Networks" Proceedings of the 3rd International ICST Conference on Body Area Networks 17, Mar. 2008, pp. 1-8 (8 pages).

Communication Pursuant to Article 94(3) EPC issued in European counterpart application No. 15839290.2 dated Apr. 18, 2019 (6 pages).

Correspondence from Japanese associate dated May 15, 2019 enclosing copy of Office Action issued in Japanese counterpart application No. 2017-513520 dated May 14, 2019 (5 pages).

* cited by examiner

METHOD AND APPARATUS FOR COMMUNICATION BETWEEN A SENSOR AND A MANAGING DEVICE

CROSS-REFERENCE TO RELATED APPLICATION

This application claims priority to U.S. Provisional Patent Application 62/050,054 entitled "METHOD AND APPARATUS FOR COMMUNICATION BETWEEN A SENSOR AND A MANAGING DEVICE" and filed Sep. 12, 2014, which is hereby entirely incorporated herein by reference.

FIELD

The disclosed method and apparatus generally relate to wireless device communication

BACKGROUND

Sensors may be used to collect real-time data of properties for an object to which the sensor is attached. Included among various applications of sensors used to collect real-time data are those associated with the collection of physiological patient data that may be used to perform medical diagnostics. For example, biosensors, which may be implanted, attached, or otherwise disposed on a patient such as on the skin, may be used to gather physiological data about a patient. That data may be wirelessly transmitted in a continuous manner and may be used to initiate medical care if an abnormal condition is detected. In some sensor systems, collected data may be selectively transmitted when triggered by detection of some condition including, for example, the detection of characteristics of abnormal patient physiology.

Particularly, where large amounts of data may be collected using a sensor and/or where a sensor is designed for long term use without recharging, it may be important to conserve energy available in the sensor including energy that may be used in associated with data transmission. Monitoring data may, for example, be transmitted to a collection station using wireless communication typically via low power radio-frequency (RF) communication. However, low-power signaling may limit the transmission range of a sensor to a specific locality. Accordingly, it may be useful to track a sensor's position to become aware of when the sensor may be moving out of that locality and a range where transmission may be effective. Tracking a sensor system may include identification of whether a sensor is communicating with another device by exchanging signals between the devices. Particularly, a message may be sent to or from a sensor and communication station with one device sending a message to another and waiting for a response. That is, a protocol for sending one or more signals or "pings" may be implemented. However, energy consumption associated with both receiving and transmitting of such signals may also be significant.

There remains a need for systems and methods that minimize the consumption of power used to track communication with a remote sensor. There is also a need for systems that may be used to transmit data based on the position of a sensor within a monitoring locale and/or to transmit data before it may be lost or become inaccessible if a sensor loses communication. For example, there is a need for systems configured to select, prioritize, and/or trigger exchange of information between a mobile device and a remote collection station as a device may approach a monitoring boundary and/or as communication strength drops.

SUMMARY

In some embodiments, a method of monitoring a patient for seizure activity may comprise: monitoring a patient for seizure activity using one or more electromyography electrodes included in a mobile sensor unit configured to collect electromyography electrode data; determining if said electromyography electrode data indicates the presence of pre-seizure motor manifestations associated with an elevated risk of having a seizure; sending exchange signals between said mobile sensor unit and a reference device in order to determine a strength of communication between said mobile sensor unit and said reference device based on either or both of a received signal strength of at least one signal among said exchange signals and a received signal quality of at least one signal among said exchange signals; sending a warning signal to a caregiver if said pre-seizure motor manifestations associated with an elevated risk of having a seizure are detected; and sending a portion of said electromyography electrode data to said reference device if both said pre-seizure motor manifestations associated with increased risk of having a seizure are detected and said strength of communication is less than a threshold level; wherein said reference device is configured to receive said portion of electromyography electrode data and queue said portion of electromyography electrode data for transmission if requested by said caregiver.

In some embodiments, a method of adjusting power consumption used to verify or track a wireless communication between a mobile sensor and a reference device may comprise: exchanging signals between said mobile sensor and said reference device during a first time period in order to determine a first strength of communication between said mobile sensor and said reference device; setting a rate of signal exchange based on said first strength of communication; exchanging further signals between said mobile sensor and said reference device during a second time period in order to determine a second strength of communication between said mobile sensor and said reference device; comparing said first strength of communication and said second strength of communication in order to determine a change in strength of communication; and adjusting said rate of signal exchange based on said change in strength of communication.

In some embodiments, apparatuses and methods herein may be configured to track whether a mobile sensor maintains communication with a managing device and to do so while conserving available system energy. In some embodiments, apparatuses and methods herein may be configured to provide data suitable to determine either or both of the position of a mobile sensor and/or a mobile sensor's proximity with respect to a reference point or boundary. And, in some embodiments, one or more system devices may execute one or more actions selectively as risk of loss of communication increases. For example, one or more system devices may selectively execute actions including prioritization, selection, and transmission of data that may be useful to an individual remotely monitoring a sensor and which may become unavailable to the caregiver if the sensor loses communication.

In some embodiments, power consumption dedicated to maintain or establish communication between a sensor and a managing device may be adjusted based on a communication strength determined for sending signals between the sensor and the managing device. In some embodiments, power consumption dedicated to maintain or establish communication between a sensor and a managing device may be adjusted based a sensor's position or proximity with respect to a communication boundary. For example, a rate or power of transmission of one or more signals dedicated to verify communication with and/or the position of a sensor may be adjusted if the sensor is known to be well within a monitoring boundary or if the strength of communication is high. In some embodiments, signals may be adjusted based on a risk of sensor boundary excursion. A risk of boundary excursion may, for example, be calculated or estimated from a sensor's position, proximity to a reference point or monitoring boundary, communication signal strength or quality, derivative value of communication strength or quality over time, and/or combinations thereof. And, when risk of boundary excursion changes, power allocated to maintain, track, or establish communication may be adjusted accordingly.

DETAILED DESCRIPTION

Figure 1A:
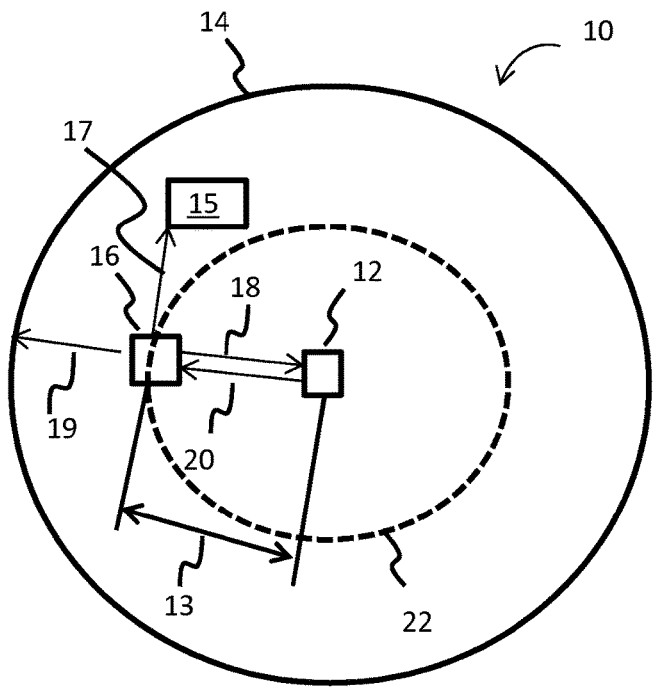
FIGS. 1A and 1B illustrate different positions of a mobile sensor with respect to a reference device in a system for coordinating or adjusting signal exchange between devices.

The following terms as used herein should be understood to have the indicated meanings.

"Computer" means any programmable machine capable of executing machine-readable instructions. A computer may include but is not limited to a general purpose computer, microprocessor, computer server, digital signal processor, or a combination thereof. A computer may comprise one or more processors, which may comprise part of a single machine or multiple machines.

The term "computer program" means a list of instructions that may be executed by a computer to cause the computer to operate in a desired manner.

The term "computer readable medium" means an article of manufacture having a capacity for storing one or more computer programs, one or more pieces of data, or a combination thereof. A computer readable medium may include but is not limited to a computer memory, hard disk, memory stick, magnetic tape, floppy disk, optical disk (such as a CD or DVD), zip drive, or combination thereof.

The term "initiation pulse" as used herein refers to one or more signals that may be sent from a device in order to verify or maintain communication between the device and one or more other devices.

The term "response signal" as used herein refers to one or more signals sent from one device in response to receipt of one or more initiation pulses sent from another device.

The term "strength of communication" as used herein means how well two devices may communicate when a transmitted signal is sent between the devices. For example, a high strength of communication means that a signal may be communicated between the devices at a detectable level or power and without significant loss or distortion of signal data content. One or more metrics may be used to express a level of strength of communication including, by way of nonlimiting example, the amplitude or power of a received signal, signal-to-noise ratio of a received signal, received signal strength indication (RSSI), link quality indication (LQI), signal quality and combinations thereof.

The term "signal quality" refers to how distinguishable a signal is with respect to a level of background noise or interference.

In some embodiments, apparatuses and methods herein may be configured to adjust characteristics of signals exchanged between system devices based on how well one device may communicate a transmitted signal to one or more other devices. In some embodiments, apparatuses and methods herein may further be configured to inform an individual of when a mobile sensor approaches a physical boundary, moves out of a communication range, is turned off, becomes damaged, or otherwise has or may become incapable of proper or reliable communication. For example, a sensor may be configured to send an audible alarm to alert an individual that the sensor is approaching a physical or communication boundary or to alert an individual that a strength or quality of data exchange has dropped below some threshold level. In some embodiments, a sensor may include a processor that may store or calculate one or more time periods that may be needed to execute one or more tasks. The processor may further be configured to determine if the sensor may be too close to a communication boundary or if communication strength is too low or dropping too rapidly to reliably or successfully execute those tasks. Appropriate actions, including, for example, preemptive transmission of data that otherwise may be at risk of becoming unavailable for successful transmission, may be executed if risk of loss of communication is deemed too great.

In some embodiments, if a remote sensor is deemed at risk of losing an ability to successfully transmit data to one or more other devices, information may be exchanged between the remote sensor and the one or more other devices to help ensure that critical data is available to system components when needed. For example, data suitable to locate the sensor, measurement data collected by a sensor, and/or other data related to sensor function, including, for example calibration data, may be organized and transmitted in order to prevent loss of data or inaccessibility of data during times when access to that data may be beneficial.

In some embodiments, the devices communicating in systems herein may operate within one or more localities. For example, in some embodiments, a device may be configured to operate within a locality including a wireless local area network (WLAN) such as WiFi. More generally, some embodiments herein may be applicable for use in systems including two or more devices wherein at least one of those devices (typically a mobile, sensor device) may be subject to varying levels of connectivity with respect to other system devices. The devices may send and receive information in a wireless manner. Wireless transmission may particularly include sending of RF signals, but methods herein may also benefit and include other systems including those that may use other transmission protocols or signaling means for information exchange. For example, some of the protocols herein may be configured for use with devices that may communicate using acoustic waves or with devices that may communicate using other forms of energy propagation.

In some embodiments, power consumption dedicated to establishing or tracking communication of system components with a sensor may be adjusted as a sensor's position or proximity with respect to a monitoring boundary changes or as communication strength between the sensor and system components changes. For example, when a sensor is comfortably within a communication boundary or when communication strength between the sensor and other system components is high, power dedicated to establishing communication with the sensor may be adjusted. For example, in some embodiments, when communication strength increases, power consumption dedicated to establishing or tracking communication of system components with a sensor may be decreased. To verify communication fidelity or strength and/or the location of one device with respect to another device or communication boundary, message signals or pulses may be sent between the devices. For example, signals may be exchanged between a mobile sensor and one or more reference devices. Exchanged signals may, in some embodiments, include one or more initiation pulses. An initiation pulse may, for example, operate with a rate or frequency based on one or more internal clock signals including, for example, signals that may be fixed or varied within a period of monitoring. In some embodiments, initiation pulses may be sent from one device without a need for the device having previously received an external signal or trigger. For example, an initiation pulse may be sent at a certain rate, and individual pulses may be sent without requiring prior receipt or acknowledging receipt of another signal. However, in some embodiments, a rate of sending initiation pulses may be adjusted in response to an external device trigger, including, for example, an externally received signal.

A device receiving an initiation pulse from another device may communicate with that other device by sending one or more return signals as part of a protocol acknowledging receipt of an initiation pulse or pulses. And, in some embodiments, an alarm or fault message may be triggered if one or more devices fail to receive some number of return signals in response to some number of initiation pulses. A device may, for example, expect to receive a return signal each time it sends an initiation pulse. However, in some embodiments and/or when a system is in a particular state, a device may send initiation pulses at some rate, but the device may only expect to receive return signals at another rate. A device sending return signals may or may not expect to receive another signal acknowledging receipt of that return signal. Some devices may initiate a fault message if they detect return signals below some acceptable rate. In some embodiments, a system may be configured to account for some rate of failure to receive and detect return signals even if a device is in range to receive and detect the return signal. For example, if a device receives and detects a return signal less than about 50% of the time or some other percentage that it sends initiation pulses, it may initiate a fault message or take other actions, including, for example, execution of recalibration or other actions designed to improve communication between itself and other system devices. In some embodiments, one or more timing sequences may be executed by a device, and if the device does not receive a return signal within the timing sequence, a fault condition may be triggered. For example, a device may start a timer, which may, for example, be a multiple of an interval between initiation pulses, and if the timer ends without the device receiving one or more return signals an alarm may be initiated. In some embodiments, a rate of sending of initiation pulses and/or rate of sending return signals may depend on how well one device receives signals from another device. For example, in some embodiments, if a received signal strength or quality of a received signal changes in one of the communicating devices, a rate of signal exchange may be adjusted.

To receive a signal, a device may include an energy transducer. For example, a device receiving a signal in the form of RF energy may include an antenna. A processor may be configured to process signals from an antenna or other energy transducer and may evaluate whether a device is receiving a signal of suitable strength in various ways. For example, a processor may gauge how well a device is receiving signals based on a percentage or ratio of signals a device detects (e.g., a device may expect to detect a certain number of initiation pulses or parts of an initiation pulse and compare the expected number to an actual detected number), based on how strongly signals are received (e.g., an amplitude or power of a detected signal), based on temporal or phase delay between two signals, based on a ratio of signal to background, based on other factors, and/or based on combinations of factors thereof. In some embodiments, a processor may evaluate how well a signal is received based on the strength of a received signal including, for example, a power level of RF energy detected at an antenna. In some embodiments, a processor may evaluate the quality of a signal received at an energy transducer. For example, to evaluate quality of signal exchange, a percentage of initiation pulses or parts of a pulse may be determined against some expected number, a signal-to-noise ratio (SNR) of detected pulses or parts of a pulse may be determined, or both. In some embodiments, a link quality indication (LQI) may be determined for exchange of signals between a remote device and a router as described in one or more IEEE protocols (such as an 802.11 and 802.15.4 specification, for example).

In some embodiments, adjustment of the power consumption of a sensor may include adjusting or setting a rate or power of transmission of initiation pulses, return signals, or both. More generally, to adjust power consumption, characteristics of signals exchanged as part of a protocol to track or verify sensor communication may be set or adjusted. In some embodiments, initiation pulses and/or return signals may be adjusted based on a risk of sensor excursion across a physical or communication boundary or otherwise based on risk of loss of communication. A risk of boundary excursion or loss of communication may, for example, be calculated or estimated using one or more processors of either or both a remote sensor and/or reference device and may include estimating or determining a sensor's position, a sensor's proximity to a reference point or boundary, a strength of communication between devices, a received initiation pulse strength or quality at either or both devices, a received return signal strength or quality at either or both devices, a derivative value of a received strength or quality over time at either or both devices, and/or combinations thereof.

In some embodiments, a processor may be configured to calculate a scalar or vector value associated with a distance that a sensor may traverse. That calculation may include use of information associated with a sensor's acceleration, velocity, position, and/or other factors and combinations of factors thereof. Information used by a processor may, in some embodiments, be obtained by one or more other sensors or components of a sensor device that may be additional to the primary data collected by a sensor. For example, in some embodiments, together with primary sensor data associated with a patient's pulse rate, an accelerometer may send data to one or more system devices suitable to identify that the sensor and patient are moving. And, for example, if the patient is determined to be moving, risk of boundary excursion may be deemed higher than if the patient is determined to be stationary. In addition, if a patient is deemed to be stationary or stationary for some period of time, risk of boundary excursion may, in some embodiments, be deemed to be lower than if the patient is found to be moving or moving towards a communication boundary of a monitoring locale.

A system or method may, in some embodiments, include characteristics of sensor movement in a calculation for how to adjust signal exchange characteristics or properties between a sensor and one or more devices. For example, one or more factors related to sensor movement, including, for example, factors that may be of constant or varying weight, may be used in a calculation for how to adjust one or more characteristics for how signals are exchanged between a sensor and one or more other devices. In some embodiments, a system may adjust one or more characteristics related to how signals are exchanged between a sensor and other devices based on a communication strength. For example, an algorithm may relate a time period for transmission of one or more signals to one or more metrics of communication strength, including, for example RSSI, LQI or a combination of both. For example, in Equation 1, a linear combination of RSSI and LQI may be calculated and used to adjust a time between transmission of consecutive initiation pulses (Pi) as shown:

$$Pi = LQI * C_{lqi} + RSSI * C_{rssi} \quad \text{(Equation 1)}$$

Where:
Pi=The interval in time between consecutive initiation pulses
LQI=the current LQI (0-100)
RSSI=the current RSSI in dBm
$C_{lqi}$=Linear LQI coefficient
$C_{rssi}$=Linear RSSI coefficient As shown in Equation 1, linear coefficients may scale the relative contributions of the above LQI and RSSI metrics of communication strength to a time interval between consecutive initiation pulses. In the above example, if the LQI is high, then the interval between transmission of consecutive initiation pulses may also be high. Likewise, if the LQI decreases, the duration between consecutive initiation pulses may tend to decrease. Similarly, if the RSSI is high, then the interval between consecutive initiation pulses may also be high. Likewise, if the RSSI decreases, the duration between consecutive initiation pulses may tend to decrease. Generally, if the duration period between consecutive initiation pulses increases, power consumption may be decreased. For example, in some embodiments, a system radio may be turned off for longer periods of time as the duration period between transmissions increases.

In some embodiments, the time interval Pi may be further adjusted based on movement information, such as shown in Equation 2:

$$Pi = [LQI * C_{lqi} + RSSI * C_{rssi}] - [C_v * v] \quad \text{(Equation 2)}$$

Where:
Pi=The interval in time between consecutive initiation pulses
LQI=the current LQI (0-100)
RSSI=the current RSSI in dBm
$C_{lqi}$=Linear LQI coefficient
$C_{rssi}$=Linear RSSI coefficient
$C_v$=Coefficient for adjusting Pi based on a contribution of sensor movement
V=velocity (or acceleration in some routines)

As shown in Equation 2, when a sensor is moving, the time interval Pi may be decreased because Pi is adjusted by the factor $C_v$ multiplied by the velocity (v). In some embodiments, Pi may be adjusted by determining or estimating the vector contribution of velocity that projects towards a communication boundary. For example, a monitoring locality may include zones of poor connectivity including some that may, for example, be within a larger area. In some embodiments, those zones may be known or determined. And, if a sensor is moving with a vector component towards a communication boundary marking one of those zones, Pi may be adjusted accordingly. In some embodiments, including, for example, some embodiments where the position of a communication boundary is not known, the positon of the communication boundary may be estimated. For example, a communication boundary may be estimated by determining a derivative value for LQI or RSSI. For example, if RSSI is decreasing over time it may be estimated that a sensor is moving towards a communication boundary. Therefore, even if a sensor is placed in a new locale or placed in a locale where the boundary for monitoring is not known or poorly defined, movement data including acceleration and/or velocity may still be incorporated in a method of adjusting signal exchange characteristics. As shown in Equation 2, movement information may be incorporated as a term that varies linearly with velocity or speed. In some embodiments, movement data may be adjusted in other ways. For example, an equation for adjusting Pi may include one or more terms associated with movement that may depend linearly or nonlinearly with acceleration or velocity. For example, in some embodiments, an acceleration or velocity value may be squared or subject to a higher order exponent.

A processor may, in some embodiments, estimate that a given distance, rate, or direction of travel may result in some degree of signal degradation which may be calculated empirically, estimated, and/or may be determined by applying one or more models including, for example, models for how electromagnetic energy may dissipate or spread when propagating through a homogenous or inhomogeneous medium. For example, in some embodiments, the intensity of an electromagnetic wave, which may be related to communication strength, may be assumed to vary as the distance squared from a point. In some embodiments, a loss of communication strength over distance may consider various other factors modeling how a signal may degrade when transmitted through a medium. For example, electromagnetic energy, when propagating through space, may not only diminish in intensity, but spatial and temporal coherence of data may likewise generally deteriorate. In some embodiments, a distance may be calculated and a model for how a signal may degrade may include calculating one or more possible paths for the sensor. For example, a trajectory for a sensor or locus of points associated with possible trajectories may be calculated and signal degradation for one or more trajectories may be calculated.

A system may, in some embodiments, integrate movement data into an estimate of risk of communication loss between a sensor and reference device. For example, the system may adjust one or more characteristics of signal exchange between the sensor and the reference device by calculating, for example, a trajectory for the sensor or locus of points associated with possible trajectories and how likely it may be that the trajectory or the locus of possible trajectories for the sensor may traverse a communication boundary. A communication boundary may be estimated or empirically known. For example, a boundary may be estimated in two dimensions to comprise a roughly circular area as may be predicted for an electromagnetic field spreading in an isotropic manner through a uniform medium. Other sensors may be free to move substantially in three dimensions, and one or more boundaries and/or trajectories may be characterized in three dimensions and/or with spherical coordinates. In some embodiments, a boundary may also be empirically measured or updated based on data for communication strength collected during monitoring. A boundary may, for example, include zones or regions of poor connectivity, and in some embodiments, the relative position of those zones may be incorporated into a calculation of whether a sensor may be likely to enter such a zone in a given time period.

In some embodiments, more than one routine may be executed as part of establishing overall risk of communication loss and/or adjusting settings for communication exchange between a sensor and other device components. For example, one routine may estimate risk of loss of communication based on derivative values of RSS, LQI or both factors of communication strength. A second routine may calculate whether a sensor may be moving towards a zone of poor connectivity. And in some embodiments, outcomes for different routines may be combined in making a decision of risk of loss of communication and/or adjustment of characteristics of communication exchange between a sensor and other device components. For example, a method may adjust characteristics of signal exchange based on which routine predicts that risk of communication loss is highest. For example, a safer approach may be selected to ensure that communication is not unexpectedly lost. In some embodiments, multiple routines may also be used to look for discrepancies in the routine outputs. For example, if a sensor tracks communication strength in one routine and another routine integrates movement data and tracks the position of a sensor within a communication boundary, it may be found that the two routines fail to agree to some expected degree. Such a finding may, for example, be used to identify problems with a sensor including, for example, various system problems including, for example, uncertainty in calibration of a transmitted signal or unexpected changes to the network such as an increase in noise or interference.

Some of the embodiments herein may be particularly useful as a means to extend the battery life of mobile sensors including those with inherent size limitations and/or where significant power may be expended in processing and/or transmission of data. For example, some biosensors, including some biosensors configured for electromyography, may more accurately detect certain physiological conditions when the sensor collects data at high rates, tracks changes in physiology over extended periods of time, or when the sensors do both. Those conditions may place significant demands on available power resources, and available energy for communication with remote devices may be particularly limited. In addition, it may be useful to send a caregiver data suitable to identify trends in the data. For example, a caregiver may want to look at a previously collected time period of sensor data (e.g., a 10 minute baseline prior to detection of a possible medical condition). That data may not be sent instantaneously and particularly, for example, as a sensor approaches a communication boundary, risk that the information may not be successfully transmitted or transmitted together with an alarm may increase. And, systems that do not track or calculate risk of boundary excursion may be at risk of losing an ability to successfully transmit either or both of an alarm and/or the aforementioned data or other useful data.

Systems described herein may, for example, warn a caregiver or patient that communication strength is low which may prompt corrective action. Moreover, the system may do so before the system loses contact or the ability to send critical data. And, if a system does lose contact with a sensor (which may occur, for example, if a patient purposefully ignores or inadvertently misses a message that they are traversing a monitoring boundary) the system may, in some embodiments, have automatically taken action to update a monitoring caregiver with certain information. For example, unlike some other systems, in some embodiments of systems herein, an individual monitoring a remote sensor may not simply receive a fault message that communication was lost with a sensor without other support information and/or warning.

For example, if a processor determines that in a scenario (such as a likely or worst-case scenario) that a sensor may lose connectivity in about 1 minute, it may adjust a rate of signal exchange so that the time between transmissions is less than 1 minute or less than 1 minute by some margin or factor. Therefore, the system may, in some embodiments, be able to alarm for either a detected abnormal sensor condition or for a missing exchange signal within the interval between signal exchange. In some embodiments, a system may set a time between transmissions as appropriate so that within an exchange interval a remote device may successfully transmit both an alarm and also calculate and transmit a sensor location. In some embodiments, a device may set a time between transmissions as appropriate so that within an exchange interval a device may successfully transmit both an alarm as well as baseline data to assist an individual to understand the state of the sensor before it was lost or out of a reliable communication range. In some embodiments, a sensor may adjust Pi using calculations based on communication strength. In some of those embodiments, a separate routine may calculate one or more predicted times to reach a boundary or zone of poor connectivity. That time may be used to determine if one or more operations (including those described above) may be executed. Therefore, a calculation of one or more scenarios of time for a sensor reaching a boundary or losing communication may adjust Pi and trigger preemptive routines for guaranteeing availability of data or Pi may be adjusted using another routine and the calculated time may be used to trigger one or more routines (e.g., preemptive routines as described herein).

In some embodiments, if a processor determines that in a scenario or worst-case scenario a sensor may lose connectivity with other system components in some time, and if available or expected available bandwidth in the near future would prevent key data from being transmitted to a caregiver in that time, the system may automatically warn the patient and/or caregiver or automatically begin sending key data to system components for reliable transmission to a patient and/or caregiver if needed. For example, a system may send or queue information for reliable transmission if a sensor baseline is elevated or otherwise shows initial signatures of abnormal qualities such as physiological data that may indicate a certain medical condition. A processor may further automatically select and prioritize data that may be useful, and in some embodiments, a caregiver may have control of how that data is prioritized. For example, calibration data, baseline data, data suitable to locate a sensor, and/or other data including compressed physiological data associated with any of the preceding forms of data may be prioritized and/or selected for transmission in some embodiments. A remote sensor may organize and/or buffer information that may be sent to a caregiver even if that information may not be ultimately sent. For example, in some embodiments, data may be maintained in a unit of memory that may be readily sent for transmittal if it is deemed necessary to do so. In some embodiments, data that may be sent in a preemptive step (e.g., sent in response to a possible boundary excursion) may be compressed. Moreover, in some embodiments, a level of compression may be selected based on the time to reach a boundary.

In some embodiments, a system may be tailored for use with a patient likely to traverse a boundary and/or not to not respond to a system warning that they have traversed the boundary such as a young child. A system may, for example, conserve useable energy by adjusting a rate of signal exchange and may also be equipped to identify times when the patient may be likely to traverse the boundary. In response to that identification, the system may send information to a caregiver to help the caregiver decide on an appropriate action. For example, if the individual is a patient, it may be undesired to have an ambulance sent each time communication is lost. And, a caregiver may want to have access to baseline data for the sensor at time periods before the sensor loses communication so that the caregiver may consider that information prior to deciding on a course of action.

In some embodiments, a sensor may be a biosensor that may be disposed on or near a patient's body, including, but not limited to, the patient's skin. By way of nonlimiting example, a sensor may be configured to monitor any of various properties or phenomena that may be associated with a biological tissue including temperature, pressure, analyte concentration, electrical, optical, magnetic, and/or other properties or phenomena. For example, in some embodiments, a sensor may include one or more electrodes that may be configured to detect electrical manifestations such as current or voltage related to activation of muscle fibers as may be used to perform electromyography. In some embodiments, a sensor may be part of a device or group of devices that may be configured to execute or trigger execution of one or more tasks such as stimulation of biological tissue or the release of a therapeutic composition or analyte. For example, in some embodiments, a sensor may communicate with a Vagal Nerve Stimulator or may be configured to trigger activation of other stimulating devices that may be used to abort, attenuate, or treat a seizure. In some embodiments, tasks may only be executed or preferred to be executed when a remote device is communicating with a managing device.

A sensor may include a source of energy such as a battery suitable to provide electrical energy as may be needed for sensing tissue properties, execution of one or more therapeutic functions or tasks, and for accommodating other sensor activities including signal transmission. A sensor may further include one or more microprocessors or other electrical circuits suitable for controlling functional elements of the sensor including by use of digital or analog methods. And, in some embodiments, the sensor may include at least some degree of processing capability as may be used to analyze collected physiological data. For example, a sensor may be a "smart" sensor having some data processing and storage capability. In some embodiments, a simple sensor may be connected via wire or wirelessly to a battery-operated transceiver mounted on a belt worn by the person. In some embodiments, the sensor may directly include a transceiver. And generally, where reference is made to a transmission or receipt of one or more signals from or to a sensor or sensor unit, a transceiver may be directly incorporated within a sensor's housing or otherwise associated with the sensor as described herein. In some embodiments, a sensor may also include one or more display elements configurable to display information to the patient or to a local caregiver in the patient's proximity.

In some embodiments, a sensor may be configured to collect electromyography data at a suitable rate to track a signal associated with electrical motor manifestations present in one or more frequency bands of data within a range of frequencies extending up to about 100 Hz, about 150 Hz, about 250 Hz or about 400 Hz. The sensor may further integrate signal in one or more bands within that range over integration windows that may be as short as about 50 milliseconds. The sensor may be configured to execute various tasks including some that may put strain on available power resources. In some embodiments, electromyography data may be collected together with information suitable to verify the position and/or connectivity of a mobile sensor disposed on a patient's muscle. In some embodiments, that mobile sensor may further be configured to send up to about 10 minutes of EMG signal data, other information associated with sensor performance and/or calibration, and a plurality of alarms or warning messages associated with abnormal physiological conditions without being recharged for periods of at least about 24 hours.

In some embodiments, it may be desirable to maintain the location of a sensor or sensor unit within certain proximity to a reference point or near a given position with respect to a reference point. For example, it may be desirable to maintain the position of a sensor with respect to a network access or other reference point. In some embodiments, a reference point may be the location of a reference device. A reference device may, for example, be a suitable device configured to collect a transmitted signal, and by maintaining suitable proximity to a sensor the sensor may maintain functional communication within a local or other network. Moreover, because a reference device may be linked to other devices via wired or wireless communication, a sensor within suitable proximity to a reference device may also maintain functional communication with one or more caregivers who may be at a distant from a monitoring locale. In some embodiments, a reference device may be a router that is suitably equipped, for example, to send data packets to other components of a monitoring system. A router may transmit data to another computer device that may be configured to perform processing functions as described herein. For example, a router may act to shuttle signals to a managing device. In some embodiments, a managing device may also act as a receiver of RF signals; that is, a reference device may itself be a managing device or be in communication with a managing device. A managing device may be configured to execute any of various processing functions as described in embodiments herein, including, for example, processing of signal data and determination of when a sensor may be approaching a boundary. In some embodiments, a managing device may also be configured to warn or initiate warning of an operator who may be local or remote from the device that the sensor may be out of range. In some embodiments, a reference device may act to shuttle signals from a part of a wireless network to another managing device such as a base station suitable for processing of EMG signals. Base stations are, for example, described in Applicant's U.S. Pat. No. 8,983,591 and U.S. patent application Ser. No. 13/542,596 which are incorporated herein by reference.

In some embodiments, a managing device or base station may be small enough to be moved to a desired location such as near a caregiver. For example, the managing device may be a portable device including an installed program suitable for execution of various tasks including, for example, receiving, sending, analysis, and display of information provided from a sensor. In some embodiments, the managing device may be a cell phone or other portable device including a suitable installed program. A managing device may also comprise a desktop computer or other device that may be more stationary than an easily portable device. A managing device may be powered by a typical household power supply and contain a battery for backup, may have more processing, transmission, display and analysis power available for its operation than may a sensor, may be able to store a greater quantity of signal history, and evaluate a received signal against that greater amount of data. A managing device may further be configured to communicate with one or more other local or remote devices. For example, a managing device may be connected wirelessly and/or via a wire connection to a network.

In some embodiments, a sensor may be equipped to monitor the physiological condition of a patient who is at risk of developing a medical condition, and the managing device may be positionable near a local caregiver who may monitor the status of the patient. The caregiver may desire to be close enough to the patient so that the caregiver may provide medical care or assistance to the patient should such care be needed. In that light, a monitoring range may be defined by the distance over which signals may be wirelessly transmitted, but may also be a more limited boundary. For example, in some embodiments, a caregiver may define a monitoring boundary based on additional preferences and/or concerns over patient safety. For example, a caregiver may want to be informed when the patient is not within a certain proximity which may be the same or different than a distance over which the sensor and managing device may exchange data. By way of example, in one embodiment, a caregiver may be a family member of the patient (such as a patient's parent), and the sensor and managing device may operate outside of a medical facility such as at the patient's home. In other embodiments, the sensor may be disposed on a patient at a managed care or residential facility and a managing device may be configured to provide monitoring data to a medical caregiver such as a doctor or nurse, and the devices may be configured to operate within the locale of the facility which may, for example, be a hospital or nursing home.

The locality in which a sensor or sensor unit may be designed to operate may be a personal network. For example, a personal network may include at least one reference device and/or network access points. An administrator for the personal network may work with the patient or caregiver of the patient to setup and control functional settings and selection of protocols for the network. Devices included in or operating in the network may, for example, use one or more communication protocols associated with device communication or handshaking established for personal area networks. For example, in some embodiments, handshaking of devices in a local area or local area network may include use of any of various IEEE protocols. And, in some embodiments, initiation pulses and responses as described herein may be integrated along with or in addition to other signals used in execution of the aforementioned protocols.

In some embodiments, a sensor may be equipped to move between both a personal network and one or more other networks. And, in some embodiments, it may be convenient to apply different protocols for locating sensor devices and/or establishing device communication depending upon whether the sensor is within the domain of a personal network and/or one or more other networks. For example, at least in some embodiments, a mobile sensor may operate primarily by sending initiation pulses when in one network, but when in another network the mobile sensor may switch to operating partially or exclusively as a responder (sending response signals). Moreover, a processor may determine that when in one locality or network or at one position in the locality or network that it is more energetically efficient to operate in one of several possible modes. In some embodiments, a mobile sensor may switch to primarily being a responder if it is in a personal network and is found to be stationary. And, in some of those embodiments, the mobile sensor may be configured to enter a sleep or power conservation mode if certain conditions are met. For example, in some embodiments, a mobile sensor may enter a mode where it may receive initiation pulses at one rate, but only respond to a small number of those pulses. A tracking routine or other routine may trigger initiation of a sleep or power conservation mode. For example, if communication strength is suitable and has not changed for some period of time and/or if a sensor is known to be stationary or to have been stationary for some time, a device may enter a sleep or power conservation mode.

In some embodiments, apparatuses described herein may be configured to send an alert that a boundary is being approached. More generally, in response to a movement near a boundary, one or more system operations may be executed. And, in various embodiments, any of a number of system apparatuses including, for example, one or more mobile sensors, associated devices in communication with the one or more sensor, object to which a sensor may be disposed, reference device, managing device, other device, or combinations thereof may be involved in execution of operations triggered in response to an identification that a sensor may be moving towards a boundary.

For example, in some embodiments, including where a sensor may be a biosensor disposed in communication with an individual or patient, an audible or other recognizable alarm may be initiated by the sensor or sensor unit if a boundary is approaching. In some embodiments, a sensor may transmit one or more portions of collected data when approaching a boundary. For example, a sensor or sensor unit may store in memory data collected during an operating period. It may be anticipated that the data may be collected and sent to permanent storage or review at a certain time such as when a sensor battery is recharged or replaced. And, that data may be most effectively transmitted or downloaded when the sensor or sensor unit is close to a managing device, network access point, or wired connection. For example, a wired connection may be established during times when a sensor unit's battery is recharging. In addition, when close to a managing device, a remote device may communicate data to the device using only low transmission power. And, in some embodiments, a system may routinely send baseline or other calibration data to a managing device including, for example, on some schedule. In some of those embodiments, a device may be programmed to send calibration, baseline or other data at some times but not at other times. For example, a device may send data when communication strength is high and where the data may be sent using only very low transmission power. That is, if within a certain time window the device is far from a managing device, the device may be configured to wait (at least for some time), and if communication strength improves, the device may then send scheduled calibration or baseline data. And, because the device waited for improved strength of communication, it may send the data at a lower power than would have been needed if the system would not have delayed transmission. To that point, in some embodiments, there may be at least some flexibility for when a sensor may send regular calibration data (e.g., it may be sent within regular windows of time, but within an individual window it may optimize transmission to conserve power).

In some embodiments, if a sensor unit is at risk of crossing a monitoring boundary and/or if there is risk that available memory may be exceeded or otherwise that stored information may not be recovered or available when needed, the sensor unit may be triggered to transmit data to a managing device. In some embodiments, as a sensor approaches a boundary, the rate at which a sensor transmits initiation pulses may be increased and/or a rate at which a sensor unit receives responses may be increased. Therefore, tracking data may be updated more frequently as risk of boundary excursion increases. And, for example, a patient may be informed without delay when a sensor traverses or may be expected to imminently traverse a boundary.

In some embodiments, various responses or combinations of responses may be executed by a managing and/or reference device based on whether a sensor may be approaching a boundary. For example, an audible or other response suited to gain the attention of an individual near a managing device may be made. In addition, an individual expected to be monitoring the managing device may be warned. The individual may, for example, be in the vicinity of the device and may be warned by an audible or other system response. Furthermore, the individual may be at a distance from the device and may be contacted accordingly such as by sending an appropriate alarm to a cell phone, pager, or other mobile device. In some embodiments, as a sensor approaches a boundary, the rate at which a managing device transmits initiation pulses may be increased.

In some embodiments, a sensor may be a biosensor that collects physiological data associated with a patient including those associated with medical conditions that may establish that the patient needs medical care. For example, in some embodiments, physiological data may be collected and may establish the presence of a condition that may demand immediate medical attention and an emergency response. However, some conditions may, at least initially, manifest as only weak physiological signatures including signatures that may be difficult to detect. And, for many conditions, the earliest signs of abnormal physiological activity are those that may be most likely to be mis-interpreted as false detections. It may be desirable to warn a caregiver that such initial signatures are present, but because risk of false detection may be significant, an emergency alarm may not always be desired. Furthermore, if, for example, a caregiver would benefit from examining trends in the condition over time, it may be useful to send a significant amount of data.

For example, in some embodiments, a method may include identifying pre-seizure motor manifestations that may indicate that a patient may be at elevated risk of having a seizure. A preceding period of collected electromyography data may sometimes help to determine that the patient may be approaching a seizure. However, sending large subsets of data every time the earliest signatures of abnormal activity are detected may be energetically costly. For example, depending on thresholds set for detection, some patients may exceed a threshold several times during a monitoring period, and if each time a large amount of data is remotely sent, battery life may be severely limited. It may therefore be useful to send a caregiver a warning message that initial signatures of a medical condition were detected without sending the caregiver other data and/or without automatically initiating an emergency alarm. In response to receiving a warning message, a caregiver may, in some embodiments, choose to initiate transmission of additional data as may be useful to look at trends in the data over time. A caregiver may then, for example, choose to manually initiate an emergency alarm if in the caregiver's experience the patient is at risk of suffering a medical condition such as an epileptic seizure. For example, a caregiver may choose to examine a previously collected interval of electromyography data, such as, for example, the previous 10 minutes or other desired amount of data. A caregiver may also choose to initiate such transmission if, for example, a sensor battery is fully or significantly charged (and where the baseline data may be sent without risk of imminent loss of critical power) or if they are aware of multiple warning messages over time and where risk to the patient outweighs concerns associated with expenditure of sensor energy. A caregiver or managing processor may also choose or be configured to initiate transmission of that data if the communication strength is low or decreasing and where there is risk that in the near future that data may become unavailable. And, in some embodiments, together with a warning message, a caregiver may be sent information including current battery strength and/or communication strength of a sensor. In some embodiments, one or more calculations of time for when a sensor may possibly lose communication may also be sent. For example, together with a warning message, a caregiver may receive a message that communication strength with a sensor is low or decreasing and/or an estimate of when the system may lose communication. In some embodiments, systems herein may estimate whether a portion of data may be sent within a certain time period.

In some embodiments herein, a processor may be configured to select a transmission protocol including those that may send a warning or emergency alarm. A transmission protocol may be selected based on various factors and may include a decision to send all available sensor data collected for a patient, a subset of that data, or only a message to a caregiver. A processor may select one of a number of selectable transmission protocols based, for example, on the content of collected sensor data, battery life, whether a patient is in one of various selectable or identified settings, whether a patient is in one monitoring locality or another, whether a sensor is in a state where communication with a managing device is strong or weak, other factors, and/or combinations thereof. For example, the content of collected sensor data may identify the presence of an emergency medical condition and an emergency alarm may be initiated in response, but the content of collected signal data may also identify only initial signatures of a possible medical condition. In response to detection of initial signatures of activity, a sensor may send a warning message to a caregiver or internally trigger one or more routines to further evaluate the collected signal data. For example, together with a warning message various routines may be initiated some of which may allow the condition to terminate passively without interrupting the patient or caregiver. And, in some embodiments, a system may calculate whether a warning state may conclude within a certain time period. For example, if a warning routine is triggered by initial signatures of activity, but there is risk that the routine will not complete before a sensor loses communication, one or more actions may be initiated. For example, the system may then upgrade an event as requiring an emergency protocol and not a warning protocol.

Depending on the timing between initial signatures of a medical condition and onset of an emergency medical condition, routines triggered in response to detection of initial signatures may, in some situations, last for several minutes or even longer. And, for example, if communication strength between a sensor and remote device is low or decreasing, there may be risk that data collected during a warning period may become inaccessible to the caregiver. In some embodiments herein, a sensor may be configured to automatically send an emergency alarm if initial signatures of a medical condition are detected and communication strength or quality between a sensor and managing device is low or decreasing. That is, a sensor may be configured to evaluate whether communication strength is low or dropping and in response may decide to adjust a transmission protocol. And, if, for example, the sensor identifies that it may not be able to complete a warning routine or protocol, the sensor may automatically send an alarm even without verification that initial signatures of activity are truly indicative of an emergency medical condition. In some embodiments, a sensor may be configured to query the state of a patient when communication strength drops or if risk of losing communication with a control device exceeds some threshold. And, in response to such detection, the sensor may send one or more alarm messages to a caregiver. For example, a caregiver may be sent a message that a sensor may be losing communication and that the patient has shown at least initial signatures of an abnormal state.

Routines for detection of early signs of seizure activity using EMG are described, for example, in Applicant's International Patent Application No. PCT/US14/68246 which is herein fully incorporated by reference. Therein, selective execution of one or more routines following an initial warning is described. In addition, strategies for execution of transmission protocols that may include either or both of a message of initial detection of possible seizure activity and a message in combination with a more intensive set of EMG data which may consume more energy are described. As described herein, in some embodiments, a transmission protocol for EMG sensor data may depend on whether a patient may be close to a position where monitoring may become difficult. That feature may be particularly valuable for persons who may advertently or inadvertently move outside of a monitoring area without responding to an audible or other message warning them of such; for example, a patient who is experiencing initial signatures of a seizure or other physiological state where they may become disoriented and or may or may not respond to an audible alarm that they are moving close to a monitoring boundary.

Therefore, by way of example, in response to detection of a warning signature of weak motor manifestations that may indicate initial signs of a possible seizure, a monitoring system may send a warning message between a detection device and base station. That warning may include a message that an event was detected, but may not include more extensive EMG data collected over time. However, if the detection device is known to be close to a boundary where monitoring may possibly be disrupted, an emergency transmission protocol may be initiated or if, for example, communication strength drops during a period following detection of one or more early warning signs of seizure detection, an emergency alarm may be automatically sent—even without, for example, identification of additional signs of seizure activity. In some embodiments, an EMG sensor may automatically query its state if communication strength decreases below some level. And, if, for example, one or more warning routines is in the process of executing during times when transmission decreases below some level, the device may automatically send an emergency alarm.

Figure 1B:
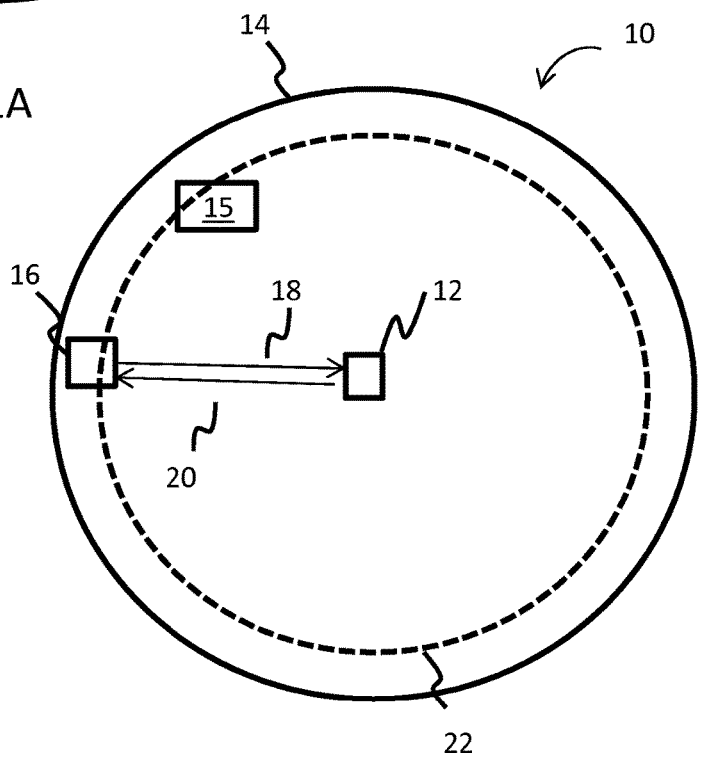

FIGS. 1A and 1B illustrate exemplary embodiments of a system 10 for coordination or adjustment of signals exchanged between two or more devices. A reference device 12 is shown near the center of a monitoring area that is within a boundary 14. A reference device 12 may, for example, be a device configured to receive signals from a mobile sensor 16 and shuttle signal data to another device or computer suitable to process and organize the sensor data. The monitoring area within boundary 14 may be a region wherein the mobile sensor 16 may transmit data to the reference device 12 with reliable signal strength. For example, in some embodiments, within the area defined by boundary 14, communication of a message that indicates the presence of an emergency medical condition may be sent and received with near perfect or suitable fidelity. The boundary 14 is conveniently shown to surround a circular suitable area, but of course, in some systems the area within boundary 14 may have any shape and may include various obstacles that may limit or shape a region where signal strength may be reliable and where wireless communication may be effective. In addition, within some monitoring locales there may be zones where communication is particularly poor or even lost. In some embodiments, zones of poor communication (such as zone 15) may be mapped within the area enclosed by boundary 14, and the relative position of a sensor 16 with respect to those zones may be incorporated in one or more calculations of risk of loss of communication between the devices 12, 16. To that point, it should be understood that the rate at which communication strength may decrease may not be the same for all communication strengths or the same for all distances from the reference device 12. And, in some embodiments described herein, methods of adjusting signal exchange rates may incorporate location data and communication strength data to more accurately predict and respond to how communication strength may change within a specific locality.

To verify or track communication between the devices 12, 16, one or more initiating pulses 18 and return signals 20 may be sent between the devices 12, 16. Device components configured for transmitting and receiving of the signals 18, 20 may be integrally connected to the devices 12, 16. For example, in some embodiments, the reference device 12 may receive initiation pulses 18 and directly send return signals 20. In other embodiments, the reference device 12 may be configured to receive initiation pulses 18, but another device may be tasked to send return signals 20. For example, that other device may be instructed to send return signals 20 by the reference device 12. That other device (not shown) may be near or at a distance from the reference device 12. Signals 18, 20 may be transmitted and received, and by detecting those signals a determination of how well the devices are communicating may be made. For example, the mobile sensor 16 may send one or more initiation pulses 18 that may be received by the reference device 12. The reference device 12 may include one or more components configured to receive initiation pulses 18. In addition, the reference device 12 may be configured to evaluate or determine a strength of communication as may include determining the quality or power of received initiation pulses 18. For example, the received strength of initiation pulses 18 may be related to the strength of transmission of the pulses 18 as well as any losses in signal energy that may have occurred in transit between the devices. When the aforementioned losses become too severe to ensure high fidelity communication, a received signal may be too low in strength to be detected or only detected at a level that indicates that communication is poor.

A signal (e.g., an initiation pulse 18) may be received by a receiver of the reference device 12 and may be analyzed using an associated processor. In some embodiments, the strength of a received signal 18 may be expressed as an amplitude or power of some magnitude. In addition, a processor may compare a signal magnitude to background levels and may evaluate a signal based on either or both of its magnitude and/or a signal to noise ratio. In some embodiments, a receiver and processor may only have an ability to determine whether a signal was received without capability to quantify its magnitude. That is, a transmitted signal or part of a transmitted signal may or may not be detected. However, in some embodiments, even if the receiver and processor are only capable of detecting the presence or absence of a given packet of energy they may still determine a communication strength or communication quality. For example, signals may be sent as a series of packets of energy and a receiver may be configured to determine based on a number of identified packets whether the signal was received with some strength or quality. For example, an expected string or series of energy packets may be transformed into bits of information by a processor. And, if some packets of energy were not received, a processor may be configured to identify one or more units of data as missing in an expected series. And, based on a pattern of detected packets of energy and/or comparison to an expected pattern, the strength or quality of transmission of a signal may then be determined. Packets or parts of a transmitted signal may be transmitted all at about the same power or with some packets varying in power as may be used to more accurately predict communication strength in some embodiments.

In response to detection of one or more initiation pulses 18, a reference device 12 may respond by transmitting or instructing another device to transmit one or more return signals 20. In some embodiments, the reference device 12 or some other device may maintain in a buffer of memory a record of the strength and/or quality of received initiation pulses over time. And, in response to receipt of one or more initiation pulses 18, the reference device 12 may send one or more return signals 20 communicating receipt of initiation pulses 18. In addition, a message instructing the mobile sensor 16 of how well previous initiation pulses 18 were detected may be sent. For example, some return signals 20 may include both a part to communicate receipt of an initiation pulse 18 and a part or message communicating the strength or quality of receipt of the initiation pulses 18. In some embodiments, a message may include information about the strength or quality of any number of previous initiation pulses 18. And, in some embodiments, that information may be used to determine various trends in signal strength. That is, the mobile sensor 16 may be communicated information about how well initiation pulses 18 were detected and changes in the strength, amplitude, or quality of detected initiation pulses 18 over time.

In response to a communication of how well initiation pulses 18 were detected, a mobile sensor 16 may adjust characteristics of transmitted initiation pulses 18. For example, if the strength of detection of initiation pulses 18 was high, risk of a mobile sensor 16 moving outside of a communication boundary may be low. And, without immediate risk of loss of communication, the mobile sensor 16 may increase a time period or interval between transmissions of initiation pulses 18. Therefore, a transmitter associated with the mobile sensor 16 may be turned off or otherwise may not be consuming power for a significant time period. Battery life may be extended accordingly. In some embodiments, other characteristics of initiation pulses 18 (e.g., in addition to periods or intervals between pulses) may also be changed or adjusted. For example, in addition (or alternatively to) changes in the duration of periods between pulses 18 the strength of transmission of pulses 18 may be adjusted. For example, in some embodiments, a sensor 16 may be capable of sending signals at various power levels. Those power levels may, for example, be made just high enough to be received by a reference device 12, but not too high to consume more energy than may be needed.

In some embodiments, the mobile sensor 16 may, in addition to or together with one or more initiation pulses 18, transmit a message informing the reference device 12 that it received a return signal 20 at some strength. For example, the mobile sensor 16 may send a confirmation message to the reference device 12 instructing the reference device 12 that it successfully received return signals 20. Therefore, at least in some embodiments, both the mobile sensor 16 and reference device 12 may be provided messages or otherwise receive information confirming that the other device successfully received a transmitted signal and/or at what strength the signal was received. Likewise, either of the mobile sensor 16 or reference device 12 may execute one or more adjustable timing routines wherein if signal from the other device is not received within some expected time period an alarm may be initiated. Therefore, if the sensor 16 is associated with a patient, either or both of the patient and/or remote caregiver may be alerted if communication strength decreases below some acceptable level or if such communication is substantially lost.

In FIG. 1A, mobile sensor 16 is shown to be well within the confines of the boundary 14. And, as described above, the mobile sensor may have knowledge that the communication strength of signals 18, 20 may generally be high. As shown by the dashed line 22, and based on a determined communication strength, the system 10 may be able to estimate that the mobile sensor 16 is some distance 13 from the reference device 12. And, at least in some embodiments, a vector defining the position of mobile sensor 16 with respect to reference device 12 may be determined or periodically determined. For example, if more than one reference device receives a signal from a remote sensor 16, the position of remote sensor 16 may be determined more accurately such as by triangulation or other mathematical procedures as used in the art. In some embodiments, position may be determined using global positioning technology, and with knowledge of the sensor 16 position, a vector may be calculated between the reference device 12 and mobile sensor 16. In addition, one or more vectors between the mobile sensor 16 and the boundary 14 (or zones within the area enclosed by boundary 14 where communication may be limited) may be determined. Therefore, the mobile sensor 16 may, in some embodiments, be aware of its location and its relative position with respect to any zones or regions where communication strength (with the reference device 12) may be limited. For example, in FIGS. 1A and 1B, a zone of poor communication 15 within the circular boundary 14 is shown. And, in FIG. 1A, the vector 17 is shown representing a distance between the sensor 16 and a zone of poor communication 15, and the vector 19 is shown representing a distance between the sensor 16 and boundary 14. In some embodiments, the relative position and shapes of boundary 14 and area 15 may be estimated or calculated and may, for example, be updated including as the sensor 16 is moved within a certain locale as may be executed as part of calibrating a locale and/or as part of patient monitoring.

In FIG. 1B, mobile sensor 16 is shown to be near boundary 14. Again, one or more initiation pulses 18 and return signals 20 may be sent between the devices 12, 16. However, communication strength between the devices 12, 16 may generally be weaker than in FIG. 1A. In some embodiments, based on determined communication strength, the mobile sensor 16 may adjust signal characteristics of transmitted initiation pulses 18. For example, when the mobile sensor 16 is well within the boundary 14 (as shown in FIG. 1A), mobile sensor 16 may, in some embodiments, transmit initiation pulses 18 at a rate of about 1 transmission every 2.5 minutes. However, when the sensor 16 is near the boundary 14 (as shown in FIG. 1B) mobile sensor 16 may, in some embodiments, send about 1 transmission every second. In other embodiments, the strength of a transmitted signal may also be adjusted. For example, the strength of signal may be minimized when the mobile sensor 16 is closer to the reference device 12.

A rate of signal transmission may be suitable to minimize risk that the mobile sensor 16 may lose communication during times between transmissions and unable to transmit data for monitoring a patient condition. In some embodiments, that risk may be based on communication strength or quality of signals 18, 20 and may include an estimate of how rapidly the signals may degrade. To estimate how rapidly a signal may degrade a derivative value of one or more metrics of communication strength may, in some embodiments, be determined. For example, a reference device 12 may communicate to a sensor 16 how rapidly the metric is changing based on any number of received initiation pulses 18. A processor included in the system 10 may further extrapolate from the derivative data when a sensor 16 may reach a certain communication strength where communication performance may be compromised. That extrapolation may include, for example, linearly extrapolating from available data of communication strength and/or derivative data of communication strength when the sensor may lose communication and/or reach a boundary. In other embodiments, nonlinear extrapolation of derivative data may be used to calculate or estimate loss of communication and/or a time to reach a boundary. In some embodiments, how rapidly a signal may degrade may be estimated from how rapidly the sensor may move (typically or in a worst case scenario)—such as if moving towards the monitoring boundary 14. In some embodiments, a monitoring system may be configured such that a sensor 16 may calculate or be communicated information about when it may traverse a monitoring boundary 14 (or border of area 15). The sensor 16 may then be aware of when a time to traverse a boundary is greater in duration or lesser in duration than a time interval (Pi) between transmissions of signals 18, 20 or when that time is lesser than some factor of the interval (Pi) as may be deemed suitable to guarantee that the sensor 16 may successfully execute one or more operations or processes before losing communication with a reference device 12. More generally, Pi may be directly adjusted based on one or more calculations of time to a boundary. Alternatively, a time scenario may be calculated, but exchange rate may be adjusted or set from communication strength. A separate routine may, in some of those embodiments, incorporate one or more calculated times to determine if one or more preemptive operations (e.g., operations in response to possible loss of communication) should be executed.

Figure 4:
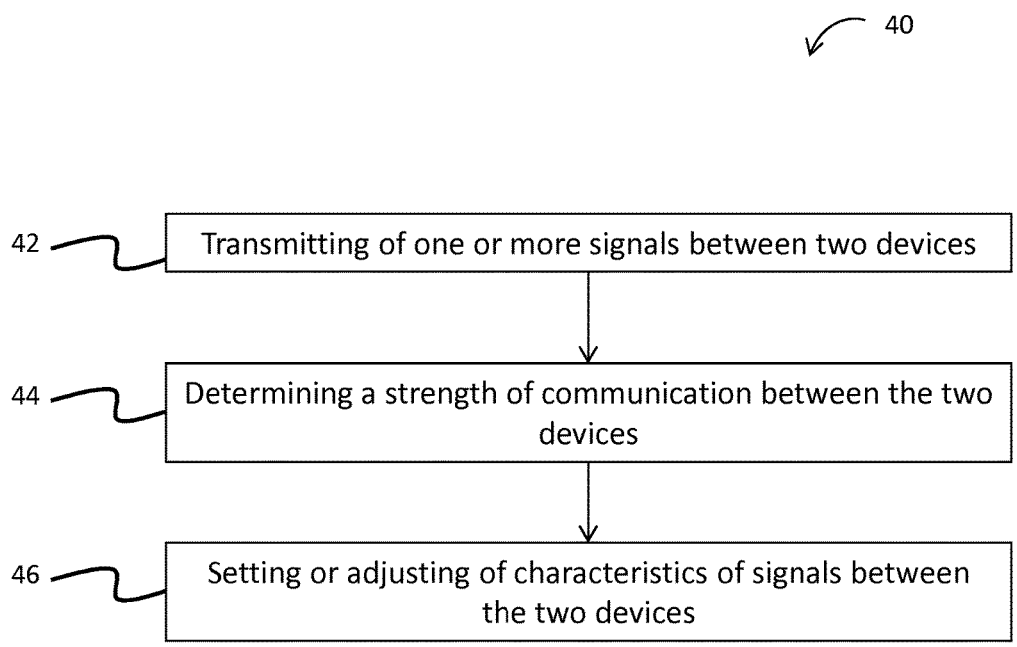
FIG. 4 illustrates one embodiment of a method for coordinating or adjusting signal exchange between devices.

For example, as also described in the method 40 of FIG. 4, a time interval (Pi) value may be evaluated from communication strength and/or determined based on one or more scenarios for how a sensor may move within a monitoring area. For example, if the sensor 16 moves from a certain position at an assumed speed towards a monitoring boundary it may do so in a certain time, and (Pi) may be accordingly adjusted. For example, in some embodiments, times between signal exchanges (Pi) or some multiple of (Pi) may not be shorter than that calculated time or some factor thereof. Therefore, Pi may be adjusted such that the system rapidly tracks sensor communication as it approaches a boundary. Likewise, the sensor may become aware when the time is lower than a time needed to execute one or more sensor tasks or operations.

Also, and again referring to the method 40, the overall bounds for Pi (e.g., between values Pi (min) and Pi (max)) may likewise be estimated or determined. That is, for a sensor 16 moving within the region defined by the boundary area 14, the system 10 may scale the interval between transmissions 18, 20 in a manner such that even if the sensor 16 moves in a worst case scenario towards a monitoring boundary it may still send transmissions 18, 20 to suitably track changes in communication strength of the devices. For example, Pi (max) may be determined based on a minimum time for a sensor to move from one region of a monitoring boundary, such as the center of the region, to the nearest edge of boundary 14 or zone of poor communication strength 15.

In some embodiments, the system 10 may scale an interval between transmissions 18, 20 linearly against one or more metrics of communication strength and/or quality. In some embodiments, the system 10 may scale an interval between transmissions 18, 20 nonlinearly against one or more metrics of communication strength. For example, as communication strength and/or quality decreases, the time interval between transmissions 18, 20 may change rapidly to guarantee that communication is not lost before the system is properly informed or able to suitably respond to that change in communication strength.

In some embodiments, additional calculations may be performed or additional metrics used to adjust properties of the transmissions 18, 20. For example, in some embodiments, the sensor 16 may be or may include an accelerometer or other device suitable to estimate acceleration or velocity. In that case, the system may, in some embodiments, incorporate knowledge of a sensor's acceleration or velocity to determine whether the device is at risk of loss of communication. For example, a sensor 16 may be communicating effectively with the reference device 12, but the sensor 16 may be rapidly moving and a higher rate of initiation pulses 18 may be sent than if the sensor 16 were not moving. Conversely, in some embodiments, it may be determined that a sensor 16 is not moving. The sensor 16 may then, in some embodiments, enter a power conservation mode, and stop sending pulses 18 or only send initiation pulses 18 at a very low rate. If the sensor 16 experiences an acceleration, the sensor may leave that power conservation mode and send initiation pulses 18 at some predefined rate or recalibrate a rate of initiation pulse 18 transmittal based, for example, on the strength or quality of one or more return signals 20.

Figure 2:
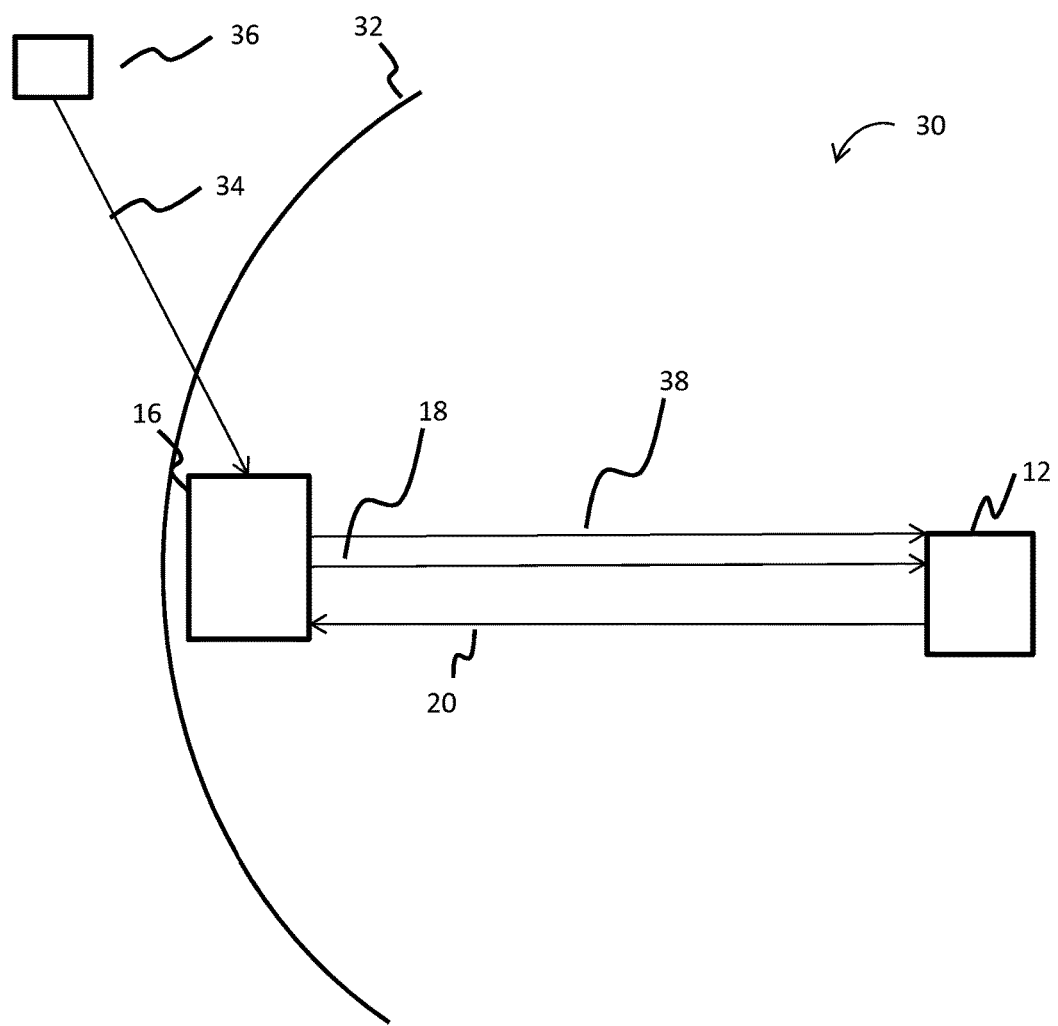
FIG. 2 illustrates another system for coordinating or adjusting signal exchange between devices.

FIG. 2 illustrates exemplary embodiments of a system 30 for coordination or adjustment of signal exchange between two or more devices. In FIG. 2, only a portion 32 of a boundary is shown for simplicity. In the system 30, the sensor 16 may be GPS enabled and may include one or more receivers suitable to detect relative strength of satellite signals 34 originating from a plurality of satellites 36 and include processing capabilities suitable to perform a calculation of its global position. Mobile sensor 16 may continuously recalculate its global position. However, in some embodiments, a sensor's global position may be determined in response to a finding that communication of signals between the mobile sensor 16 and a reference device 12 is low. For example, calculation of position may be made globally as an alternative to other procedures for location such as triangulation based on local signals if those signals are unavailable. And, to minimize expenditures of energy associated with determining a mobile sensor's 16 position, in some embodiments herein, the position of a remote sensor 16 may only be made (or that information only transmitted to a reference device 12) if risk of losing communication with the remote sensor 16 becomes significant. In other embodiments, the position of mobile sensor 16 may be calculated and/or transmitted at some frequency, but that frequency may be adjusted based on the strength of communication between the mobile sensor 16 and reference device 12.

In some embodiments, a calculation of the position of a mobile sensor 16 may be executed if the remote sensor 16 identifies abnormal physiological signatures that may be indicative of a medical state such as a seizure. In addition, the proximity of the sensor 16 to a reference position may be outside of a range where a caregiver is comfortable, and the system may be triggered to calculate the sensor's position. For example, in some embodiments, the caregiver may be a parent of a child with a medical condition and they may want to know that their child is outside of a range they may be comfortable with. The system may, therefore, include the capability for a caregiver to select a range wherein if their child exceeds a certain distance or proximity from a reference device (e.g., a base station positionable near the parent), that the parent is notified and/or notified with instructions on how to find the child.

Figure 3A:
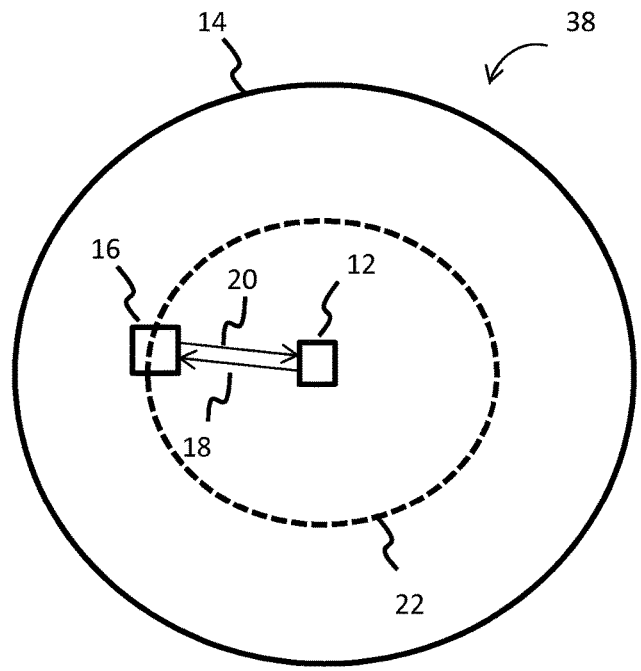
FIGS. 3A and 3B illustrate different positions of a mobile sensor with respect to a reference device in another system for coordinating or adjusting signal exchange between devices.
Figure 3B:
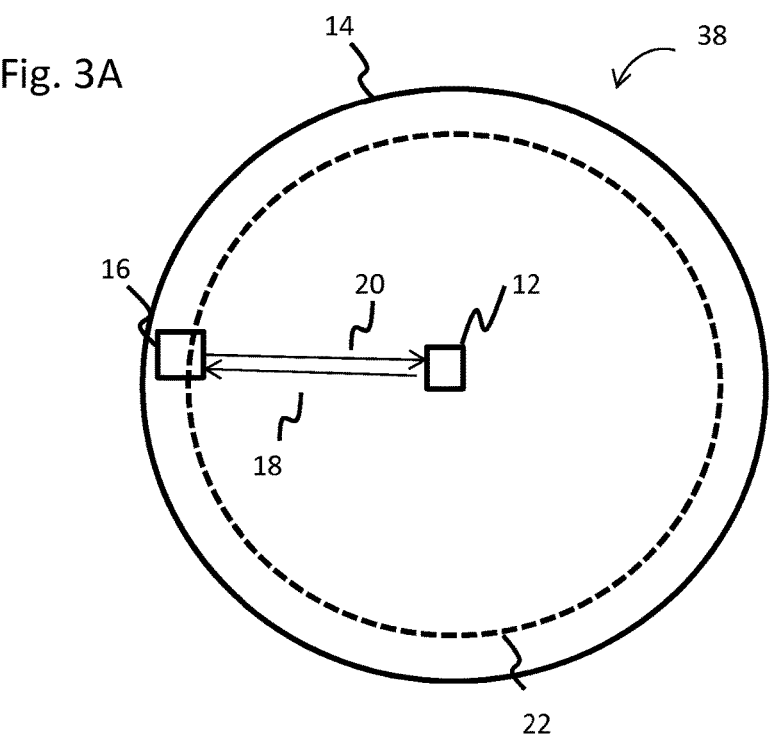

FIGS. 3A and 3B illustrate exemplary embodiments of a system 38 for coordination or adjustment of signals exchanged between two or more devices. The system 38 differs from the system 10 in that initiation pulses 18 may be sent from the reference device 12. Likewise, return signals 20 may be sent from a mobile sensor 16 to reference device 12.

In the system 38, the mobile device 16 may include one or more components configured to receive initiation pulses 18. In addition, the mobile device 16 may be configured to evaluate or determine strength or quality of received initiation pulses 18. Again, the received strength of initiation pulses 18 may be related to the strength of transmission of the pulses as well as any losses that may have occurred in transit between the devices. For example, when the aforementioned losses become too severe to ensure high fidelity communication, the signal amplitude may be too low to be detected or only detected at a level that indicates that communication is poor.

In the system 38, a mobile device 16 may send one or more return signals 20 in response to one or more initiation pulses 18. A return signal 20 may include a signal suitable to communicate to a reference device 12 receipt of the one or more initiation pulses 18. In addition, in some embodiments, a return signal 20 may include a message to inform the reference device 12 how effectively any number of previously received initiation pulses 18 were detected.

The system 38 may be configured to adjust a rate at which the devices 12, 16 exchange signals. And, generally, the system 38 may adjust a rate of return signals 20 as may be desired to minimize energy consumption for the mobile device 16. For example, in some embodiments, the reference device 12 may be configured to determine the strength or quality of received return signals 20, and in response it may adjust a rate at which it sends initiation pulses 18. Therefore, the remote sensor 16 may send return signals 20 at a rate that is accordingly adjusted. Also, while it is possible in the system 38 to determine the strength of initiation pulses 18 and a system may at some times do so, it may be desirable for the system 38 to evaluate, at least some of the time, the strength of signals as received by the reference device 12. For example, if the battery strength of mobile sensor 16 is low, then transmission strength may sometimes become less reliable. And, requiring that signals pass from the remote device to the reference device may be desired because such an operation may respond to drifts, changes or other inaccuracies in the power at which a device may send a signal such as if calibration routines associated with transmission have error or become unstable as system energy is drained. That is, such an operation demands that signal is accurately transmitted and detected as would an emergency message—e.g., it requires transmission from the remote device and receipt by the reference device.

In some embodiments, the reference device 12 may be configured to determine the strength or quality of received return signals 20, and in response it may send a message to the mobile device 16 that it only expects to receive a return signal 20 at some rate. For example, the message may instruct the mobile sensor 16 to only send return signals to every other initiation pulse 18 it receives (or some other suitable proportion of initiation pulses 18). The mobile sensor 16 may, in some embodiments, send a response to some proportion of initiation pulses 18, but if the strength and/or quality of one or more received initiation pulses 18 suitably changes, the mobile sensor 16 may then opt to send return signals 20 to a greater proportion of initiation pulses 18. Therefore, in that situation, the ratio of initiation pulses 18 and return signals 20 may be varied. Advantageously, initiation pulses 18 may be sent at a relatively high frequency. However, as long as communication strength does not change, the mobile sensor 16 may only respond with a small number of return signal transmissions 20. Thus, the battery life of the mobile sensor 16 may be conserved, but the system may still be sending messages at a higher rate.

In some embodiments, like the reference device 12, the mobile sensor 16 may also be configured to determine a received signal strength and/or quality. The mobile sensor 16 may then receive initiation pulses 18 at a high rate, but if the strength is constant or within some range, only send return signals 20 at a low rate. The reference device 12, may (as discussed above) have previously sent a message that it only expects to receive a return signal on some interval. Therefore, the devices 12, 16 may safely adjust a proportion of return signals 20 to initiation pulse 18 without one device mistakenly identifying that communication was lost. Advantageously, the strength of communication may be continuously assessed, but the mobile device 16 may still only transmit signals at a low rate conserving energy. More generally, in some embodiments, together with an initiation pulse 18 or return signal 20, one device may communicate to another a message that communication appears to be stable and that it will not send return signals 20 for some period of time as long as it is still safely receiving initiation pulses 18. And, in some embodiments, a device may instruct the other device that it is entering a power saving mode where it will only respond to detection of some initiation pulses 18. That is, a device may detect some initiation pulse without responding actively to the other device. A device may, in some embodiments, exit a power saving mode if, for example, it determines that initiation pulses 18 have decreased or changed in strength or quality. Alternatively or additionally, in some embodiments, a device may exit a power saving mode if one or more sensor or sensor components identify acceleration or movement.

In some embodiments, a reference device 12 may receive a message updating the reference device about the strength of communication as determined by the sensor 16. The reference device 12 may be configured to expect only a response some proportion of times that it sends out an initiation pulse 18. Therefore, at least in some embodiments, a number of initiation pulses 18 and return signals 20 may be different. And, for example, where a remote sensor 16 operates to send return signals 20 it may be advantageous for a system 38 to operate without a one-to-one correspondence between initiation pulses and return signals. Advantageously, a remote sensor 16 may in some embodiments of system 38 still receive initiation pulses 18 at a high rate even if it is only sending return signals at a lower rate. Therefore, the remote sensor 16 may still continuously probe whether initiation pulses are received with good strength, and if the remote sensor 16 moves rapidly towards or away from a reference point it may become aware of such without a significant delay. And, in some embodiments, it may respond to a changing strength of initiation pulses 18 by sending the return signal 20 at a lesser or greater frequency. In addition, it may send a message along with or in addition to return signals 20, the message informing the reference device 12 of the change in detected initiation pulse 18 signal strength. That message may tell the reference device to expect a change in frequency of return signals 20. And, for example, if the reference device 12 fails to receive return signals 20 at the updated rate it may deem that the remote device 16 is out of range or otherwise lost communication for some other reason.

FIG. 4 illustrates exemplary embodiments of a method 40 for coordination or adjustment of signals exchanged between two or more devices. In a step 42, one or more signals may be transmitted from one device to another. For example, in some embodiments, a remote device may send initiation pulses to a reference device. In other embodiments, the reference device may send one or more initiation pulses to a remote device. In some embodiments, a device may operate as either or both of a transmitter of initiation pulses and/or responder of initiation pulses including, for example, at different times within a period of use. In a step 44, communication strength between the communicating devices, e.g., a remote and reference device, may be determined. To determine strength of communication either device or both devices may, for example, be configured to evaluate a strength, amplitude, or quality of a received signal. In the step 46, setting or adjusting of characteristics of signals transmitted between the devices may be executed based on determined communication strength.

For example, a method 40 may comprise adjusting a rate of signal exchange if the communication strength changes. For example, a mobile sensor and reference device may begin exchanging signals at one or more default exchange rates, and as communication strength changes, that rate may be adjusted. For example, if communication strength is found to increase, a mobile device may then send signals at some reduced rate in order to adjust power consumption. In some embodiments, a power of transmission may also (or alternatively) be adjusted based on communication strength. Some devices may default to some predetermined exchange rate when monitoring begins and after determining the strength of communication of some number of signals the devices may adopt a rate of signal exchange that scales based on one or more algorithms or equations including as shown in Equation 1. A rate of signal transmission (e.g., Pi in Equation 1) may be established such that if communication strength is high, initiation pulses may be sent at a low rate conserving power and increasing battery life.

Figure 5:
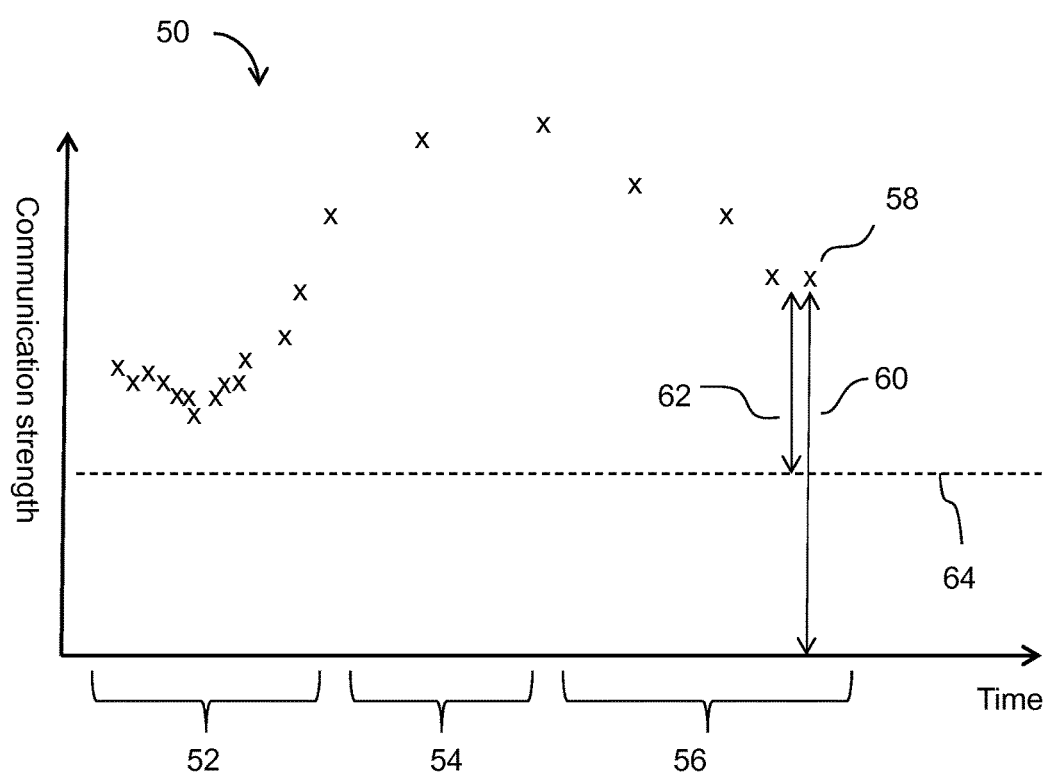
FIG. 5 illustrates a model set of data showing how communication strength may vary over time.

FIG. 5 shows a graph 50 of communication strength versus time for a model sensor and may be used to further demonstrate some of the methods described herein. As shown therein, various measurements of one or more metrics of communication strength may be made. Those measurements may, for example, be made when receiving one or more exchanged signals, and if strength is determined each time signals are exchanged, the spacing of measurements may be directly related to Pi. For example, an RSSI or LQI value may be determined by one or more communicating devices. In the graph 50, individual measurements are shown with an (x), and as shown therein, in different time periods 52, 54, and 56 the spacing between measurements (which again may be proportional to Pi) is varied. For example, within the time period 52, times between measurements is less than in the periods 54, 56. The times between measurements may be related to the communication strength and within the time period 52 the communication strength is low and it may be advantageous to send initiation pulses at a high rate; therefore, the time between measurements (and transmissions) is small. In the time period 54, the gap between measurements is relatively large as communication strength is high. As explained herein for the last measurement 58 shown, the time interval Pi may be adjusted in different ways. For example, Pi may be related to the communication strength 60 as determined at the time of measurement 58. Alternatively, the time between transmissions Pi may be related to how much greater a level of communication strength 62 may be above some minimum acceptable communication strength 64.

Figure 6:
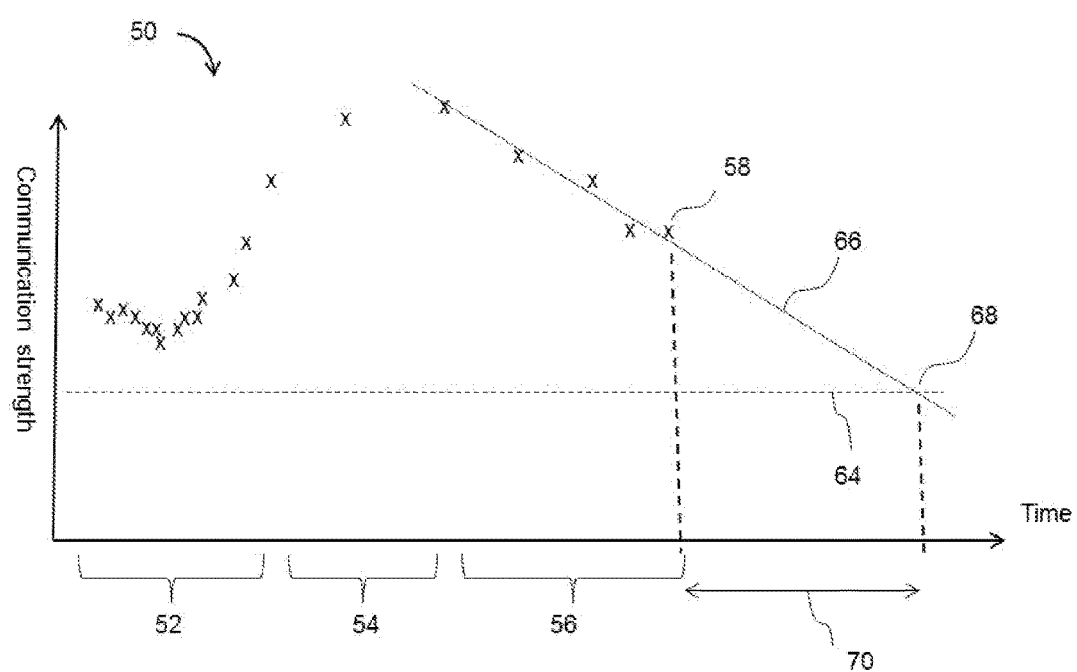
FIG. 6 illustrates the model set of data in FIG. 5 showing various aspects of how the model data may be processed in a method for coordinating or adjusting signal exchange between devices.

FIG. 6 shows the same graph 50 which again shows model data for communication strength versus time for a sensor. In FIG. 6, dashed line 66 is shown. Dashed line 66 may be calculated based on any number of previous measurements of communication strength. For example, as shown in FIG. 6, dashed line 66 may be a best fit line based on measurement data in the time period 56 (which in this example includes 5 data points of signal strength including the data point 58). Other curves that may be fit to strength data include, for example, a parabola, polynomial, or other equation. For example, in other embodiments, a curve may be a best-fit polynomial of the form $(a_0+a_1X+a_2X^2)$ where $a_0$, $a_1$, $a_2$ represent adjustable coefficients and the variable X may be one or more metrics of communication strength. FIG. 6 also shows a point of intersection 68 (i.e., the intersection between line 66 and minimum acceptable communication strength 64), which graphically represents an extrapolation of when the sensor may lose communication if communication strength continues to change as predicted by best fit line 66. That is, as shown by the length 70 (along the time axis and may define a time 70) a predicted time to when signal communication may become compromised is shown.

In some embodiments, the time between transmissions Pi may be related to the predicted time 70. For example, Pi may be scaled to be some factor that is greater than the duration predicted by line 70. That is, Pi may be related to predicted time 70. In some embodiments, a method may calculate Pi based on communication strength (e.g., as described in Equation 1) and/or one or more model functions (such as best fit line 66). For example, in some embodiments, Pi may be calculated each way and a system may choose Pi as calculated in either way. For example, a method may select the smaller value for Pi. To that point, when a sensor is rapidly moving towards a boundary, Pi calculated by the best fit line 66 (or from derivative data of signal strength or some other curve fit) may, for example, more accurately express risk of loss of communication. Thus, a method may take the safest value for Pi. In some embodiments, by calculating Pi in each way, coefficients in Equation 1 may be adjusted—e.g., the coefficients may be adjusted to generally make the average value of Pi that is calculated to be greater. Accordingly, battery life may be extended. For example, the coefficients may be adjusted because the worst case scenario for a sensor rapidly moving out of range is safely contemplated by the extrapolation. In some embodiments, Pi may be adjusted as defined by Equation 1 or another appropriate equation. A method may still estimate one or more times for possible loss of communication. And, in some embodiments, that calculation may be used to trigger execution of one or more operations associated with loss of communication. For example, the calculated time may be used to preemptively trigger transmission of key data before it is lost. In other embodiments, preemptive operations may be triggered based on the achieving of one or more thresholds of communication strength. For example, if communication strength decreases to be close to the threshold level 64, one or more preemptive operations may be executed. In some embodiments, an algorithm may calculate any combination of communication strength 60, delta value between a strength and minimum acceptable strength 64, and time predicted by line 70, and various operations such as the setting of Pi, transmission power of signals or execution of preemptive operations in response to risk of loss of communication may be based on any one or combination of the aforementioned.

In some embodiments, at the onset of a monitoring period, devices may exchange one or more of transmissions between the devices to initially gauge communication strength and to determine an initial rate of data exchange. That is, one or more devices may execute an exchange calibration procedure. And in some embodiments, that procedure may involve calculations that may be in addition to other calculations executed during other periods of monitoring. For example, more extensive and/or involved calculations of risk of loss of communication may be executed. In some embodiments, one or more exchange calibration procedures may be executed automatically if, for example, a rapid change in communication strength is identified, a device moves between localities, and/or a sensor begins communicating with a different reference device or in a different network. In some embodiments, a device may execute an "exchange calibration procedure" prior to or if it enters a power conservation mode which may be triggered, for example, if the device becomes stationary or is stationary for some period of time. In some embodiments, as part of an exchange calibration procedure, a sensor may determine its position such as by triangulation of local signals received or sent to one or more devices or using GPS technology.

In some embodiments, it may be desirable to maintain the interval (Pi) within certain acceptable bounds. For example, it may be desired to only vary the interval (Pi) between a maximum possible interval Pi(max) and a minimum possible interval Pi(min) as may be expressed by the relation:

$$Pi(max) < or = Pi < or = Pi(min) \qquad \text{(Equation 3)}$$

Where:
Pi(max)=Max possible interval
Pi(min)=Min possible interval

For example, Equation 1 or Equation 2 may vary Pi but be subject to the above constraint. Values of Pi (max) may be default values, calculated values or a combination of both. And, in some embodiments, Pi (max) may be calculated as part of an exchange calibration procedure that is run at regular intervals or based on other factors as described above. For example, a patient or caregiver may dispose a sensor on a patient at a position where connectivity is high. Also, the device may, in some embodiments, automatically execute an exchange calibration procedure if it is found that the communication strength changed significantly or rapidly including, for example, if the strength increases. Therefore, in some embodiments, a device may calculate Pi (max) when starting a monitoring period, recalculate Pi (max) such as if communication strength improves during monitoring, and/or use a default value such as may be empirically set or selected. The value of Pi (max) may, in some embodiments, be set to be about 80 seconds to about 300 seconds. The value of Pi (min) may, in some embodiments, be set to be about 1 second to about 20 seconds. If a routine or algorithm determines that Pi should be less than Pi (min) a system may, in some embodiments, issue an alarm or warning.

Figure 7:
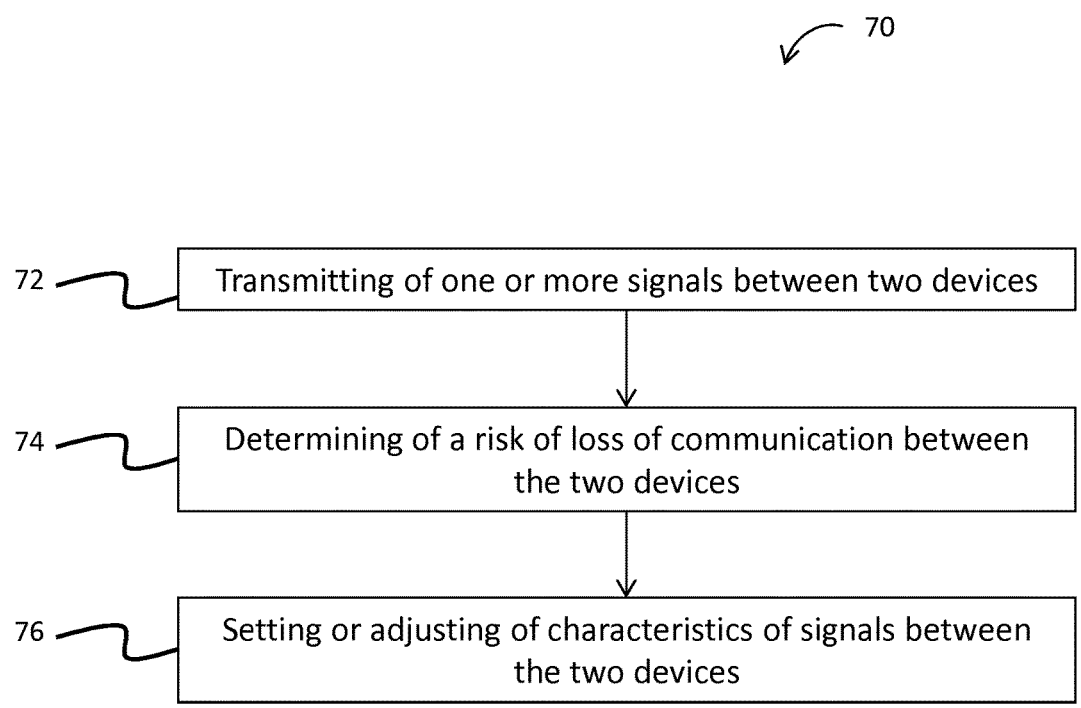
FIG. 7 illustrates another embodiment of a method for coordinating or adjusting signal exchange between devices.

FIG. 7 illustrates exemplary embodiments of a method 70 for coordination or adjustment of signals exchanged between two or more devices. In a step 72, one or more signals may be transmitted from one device to another. By way of example only, in some embodiments, a remote device may send initiation pulses to a reference device and the reference device (or other device in communication with the reference device) may transmit response signals. In a step 74, a risk of loss of communication between the devices may be determined. And, upon calculation of a risk of loss of communication, a rate of signal transmission may be set or adjusted. In some embodiments, other characteristics of signal transmission such as transmission power may alternatively or additionally be set or adjusted based on a risk of loss of communication.

In some embodiments, in the step 74, one or more routines may be executed and the routines may express metrics associated with risk of loss of communication. For example, a routine may be based on communication strength, including, for example, as expressed in Equation 1. That is, Pi as calculated therein may be related to risk (e.g., where Pi is small risk may be high). Another routine may calculate a time to loss of communication (such as described in FIG. 6) and may include execution of one or more extrapolations such as by calculating a best-fit line or other curve. As described therein, Pi may be related to that time or a factor of that time. Another routine may incorporate movement data together with information concerning the form or shape of a monitoring locale. For example, a trajectory or locus of possible trajectories may be determined for a sensor. Determining possible trajectories may involve determining the position of a sensor and estimating a rate at which the sensor may move in one or all possible directions. If the trajectory may overlap a boundary (or zone of poor connectivity) a time to reach the boundary may be determined. In some embodiments, a calculation of time for a sensor to reach a boundary may include a measured speed or velocity of a device or import a suitable or default acceleration or velocity value (such as an average or maximum velocity likely for a given sensor) into one or more equations involving speed, distance, and time (e.g., distance=(speed)(time)). Pi may be related to that time. For example, Pi may be scaled to be some multiple of the time to reach the boundary (or zone of poor connectivity). Any combination of the aforementioned routines (or other routines described herein), may be included in the step 74. In the step 76, setting or adjustment of characteristics of signals exchanged between devices may be set. For example, if a plurality or routines are executed any of the various Pi values may be selected and applied for use in one or more next transmissions of exchange signals. In some embodiments, a method may select the smallest Pi value (which may be considered the safest Pi value).

In some embodiments, risk of loss of communication may be conveniently expressed as one or more risk metrics. By way of nonlimiting example, risk of loss of communication may be related to a possible time period in which a sensor may lose communication with the reference device. For example, a time period may reflect a worst case or other scenario wherein if the sensor moves towards a monitoring boundary (which may be some estimated or determined distance away) and at some speed (which may be assumed or calculated) the sensor may move beyond the boundary in that time period. In some embodiments, distance to a boundary may be estimated or calculated (e.g., using signal strength, triangulation, or global positioning techniques) and a time period for a sensor to move that distance may be estimated. For example, an estimated speed may be related to the object to which the sensor is attached.

Figure 8:
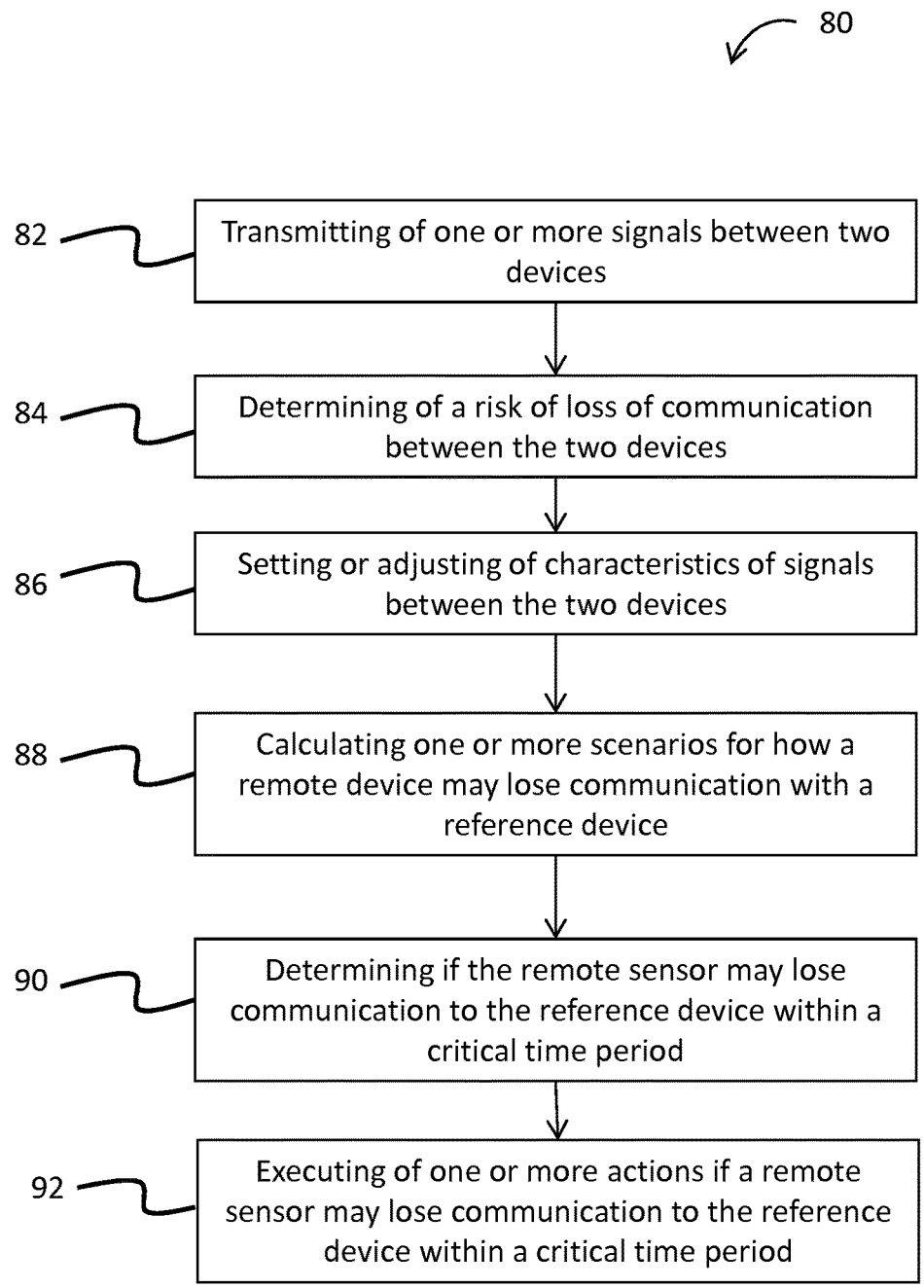
FIG. 8 illustrates a method for coordinating or adjusting signal exchange between devices and for executing one or more system responses.

FIG. 8 illustrates exemplary embodiments of a method 80 for coordination or adjustment of signals exchanged between two or more devices. In a step 82, one or more signals may be transmitted from one device to another. By way of example only, in some embodiments, a remote device may send initiation pulses to a reference device and the reference device may transmit response signals. In a step 84, a risk of loss of communication between the devices may be determined. As shown in the step 86, setting or adjusting characteristics of signals transmitted between the devices may then be executed. For example, if communication strength is found to increase, a mobile device may then send signals at some reduced rate in order to adjust power consumption.

In a step 88, one or more system devices may calculate one or more scenarios for how a remote device may lose communication with a reference device. For example, in some embodiments, determining a risk of loss of communication may include calculating a worst case scenario for a sensor moving directly towards a monitoring boundary at an assumed or calculated speed. For example, a worst case scenario may include a sensor moving directly towards a boundary or other zone of low connectivity in a minimum time period. That is, the minimum time period may be the shortest time period for the sensor to lose communication with the reference device and may be calculated as part of an analysis of the "worst-case scenario."

A calculation of minimum time to reach a monitoring boundary may include calculating the locus of points accessible to a sensor when moving for an assumed or calculated speed or velocity for a given time. Whether an assumed or calculated speed or velocity is selected may depend on whether one or more of those metrics is available. However, it may also be based on the object to which the sensor is attached. For example, some objects may generally change speed or velocity relatively slowly. Therefore, previous values of the aforementioned metrics may generally reflect future activity. Other objects may change speed or direction randomly and it may be suitable to apply a model where any of various directions of travel may be assumed. A locus of accessible points may be compared to positions within a known or estimated monitoring area including regions of poor connectivity. For example, it may be known that signal quality is insufficient or unreliable in some areas of a personal network either because the areas are near a limiting distance from a reference point or because the area is prone to interference. And, if, for the given time, a locus of accessible points first extends into those areas or extends at some probability, that time may be treated as a minimum time for loss of communication.

In some embodiments, risk of loss of communication may also be related to other metrics in addition to minimum times for loss of communication. For example, over time it may be found that communication strength has become erratic or otherwise shows trends or behaviors that may be inconsistent with a sensor moving within a monitoring locale. Those signatures may by themselves be used to determine that risk loss of communication may be significant. In some embodiments, a processor may examine whether trends in communication strength are consistent with strength values predicted for movements within a locality and if trends in strength are not consistent with those predicted, risk may be deemed high or a fault message may be issued.

In a step 90, one or more system devices may calculate if a time period (such as a minimum time period in a worst-case scenario) may be shorter than some critical time period. For example, a critical time period may be a time for a device to take some action to correct its trajectory and avoid loss of communication. A critical time period may also include a time period to transfer data that may be useful to a caregiver or other person monitoring a remote sensor. For example, in some embodiments, it may be desired to calculate the position of a sensor before it loses communication, and a critical time period may reflect a necessary time to calculate a sensor's position and successfully communicate that position to a managing device. A critical time period may also include a time period to successfully run one or more warning routines. For example, in some embodiments, a warning routine may be initiated if motor manifestations show abnormal signs of muscle activity as may be indicative of a pre-seizure state. Such routines may, in some embodiments, last for a duration period of up to about 30 seconds or up to about 10 minutes. And, in some embodiments, the duration of a warning routine may be compared to a time period (such as a minimum time period in a worst-case scenario). If that time period is less than the duration of a warning routine, one or more system actions may then be executed (step 92).

In a step 92, one or more actions may be executed if a time period is shorter than the time needed to execute one or more critical system operations. That is, if a remote device is deemed at risk of losing communication before a relevant operation may be completed, the system may take action. For example, if the duration of a warning routine is longer than a time period wherein a sensor may lose communication with a managing device, one or more transmission protocols may be executed. For example, an emergency protocol may be executed instead of a warning message if there is significant risk that loss of communication may occur. Critical system operations may further include, by way of nonlimiting example, sending of relevant baseline or calibration data, processing and transmission of global position information, execution of one or more monitoring routines, other processes, and combinations thereof.

Although the disclosed method and apparatus and their advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. For example, any feature described for one embodiment may be used in any other embodiment. Use of the word "include," for example, should be interpreted as the word "comprising" would be, i.e., as open-ended. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

What is claimed is:

1. A method of adjusting power consumption in a body-mountable mobile sensor including one or more electromyography electrodes configured for collecting electromyography data for a patient, the mobile sensor in wireless communication with a reference device, the method comprising:
    providing a body-mountable mobile sensor, the mobile sensor including one or more electromyography electrodes for collecting electromyography data for a patient, said mobile sensor in wireless communication with a reference device, said mobile sensor having a level of power consumption dependent upon a transmission rate of signal exchange between said mobile sensor and said reference device;
    exchanging first signals at a transmission rate of signal exchange between said mobile sensor and said reference device during a first time period in order to determine a first strength of communication between said mobile sensor and said reference device;
    exchanging second signals between said mobile sensor and said reference device during a second time period in order to determine a second strength of communication between said mobile sensor and said reference device;
    comparing said first strength of communication and said second strength of communication in order to determine whether strength of communication has increased or decreased;
    increasing said transmission rate of signal exchange in response to determining that said strength of communication has decreased; and
    decreasing said second transmission rate of signal exchange in response to determining that said strength of communication has increased.

2. The method of claim 1 wherein the determining of said first strength of communication and said second strength of communication includes calculating at least one of a received signal strength and a received signal quality.

3. The method of claim 1 wherein the exchanging of first signals between said mobile sensor and said reference device and the exchanging of second signals between said mobile sensor and said reference device comprises:
    transmitting one or more initiation pulses from said mobile sensor to said reference device; and
    transmitting one or more response signals from said reference device to said mobile sensor in response to a detection of said one or more initiation pulses by said reference device.

4. The method of claim 3 wherein said first strength of communication and said second strength of communication are calculated based on at least one of a received signal strength and a received signal quality of said one or more initiation pulses.

5. The method of claim 4 further comprising sending an adjustment signal from the reference device to the mobile sensor to trigger adjustment of said second transmission rate of signal exchange.

6. The method of claim 1 wherein said reference device is a portable base station.

7. The method of claim 1 further comprising:
    determining a duration of time corresponding to when said mobile sensor and said reference device may lose communication;
    comparing said duration of time corresponding to when said mobile sensor and said reference device may lose communication to a second duration of time suitable for transmitting a portion of sensor data collected using said mobile sensor; and
    transmitting a portion of said electromyography data to said reference device in response to determining that said second duration of time is less than said duration of time corresponding to when said mobile sensor and said reference device may lose communication.

8. The method of claim 7 wherein said duration of time corresponding to when said mobile sensor and said reference device may lose communication is an extrapolated value derived from data for communication strength over time.

9. The method of claim 7 wherein said portion of said electromyography data is associated with a detected seizure.

10. The method of claim 7 wherein said portion of said electromyography data is associated with pre-seizure motor manifestations that may indicate that a patient is at an increased risk of having a seizure.

11. A system for monitoring a patient for seizure activity and adjusting power consumption used to verify remote connectivity between a mobile sensor and a reference device, the system comprising:
    a body-mountable mobile sensor, the mobile sensor including one or more electromyography electrodes for collecting electromyography data for a patient, a radio configured for sending exchange signals originating from said mobile sensor, and a battery for providing a source of power for operating said radio, the battery having a charge level dependent upon a level of power consumption in said radio;
    one or more reference devices configured for sending and receiving exchange signals with said mobile sensor in order to verify remote connectivity between said mobile sensor and said one or more reference devices;
    wherein either or both of said mobile sensor and said one or more reference devices comprise a processor configured to:
        determine a first strength of communication by processing exchange signals transmitted between said mobile sensor and said reference device at a transmission rate of signal exchange during a first time period;
determine a second strength of communication between said mobile sensor and said reference device by processing exchange signals transmitted between said mobile sensor and said reference during a second time period;
compare said first strength of communication and said second strength of communication in order to determine whether strength of communication has increased or decreased;
increasing said transmission rate of signal exchange in response to determining that said strength of communication has decreased; and
decreasing said transmission rate of signal exchange in response to determining that said strength of communication has increased.

12. The system of claim 11 wherein said one or more reference devices is a portable base station.

13. The system of claim 11 wherein said processor is part of said mobile sensor.

14. The system of claim 11 wherein said processor is part of said one or more reference devices.

15. The system of claim 11 wherein said processor is further configured to determine a duration of time corresponding to when said mobile sensor may lose communication with at least one of said one or more reference devices.

16. The system of claim 15 wherein said duration of time corresponding to when said mobile sensor may lose communication with at least one of said one or more reference devices is an extrapolated value derived from data for communication strength over time.

* * * * *